United States Patent [19]
Budt et al.

[11] Patent Number: 5,629,431
[45] Date of Patent: May 13, 1997

[54] INHIBITORS OF RETROVIRAL PROTEASES

[75] Inventors: Karl-Heinz Budt; Anuschirwan Peyman, both of Kelkheim(Taunus), Germany

[73] Assignee: Hoechst Aktiengesellschaft, Frankfurt am Main, Germany

[21] Appl. No.: 479,562

[22] Filed: Jun. 7, 1995

Related U.S. Application Data

[63] Continuation of Ser. No. 293,112, Aug. 19, 1994, abandoned, which is a continuation of Ser. No. 167,613, Dec. 16, 1993, abandoned, which is a continuation of Ser. No. 627,818, Dec. 14, 1990, abandoned.

[30] Foreign Application Priority Data

Dec. 16, 1989 [DE] Germany .................. 39 41 607.0
Jun. 13, 1990 [DE] Germany .................. 40 18 942.2

[51] Int. Cl.$^6$ ...................... C07D 209/04; C07F 9/28
[52] U.S. Cl. ...................... 548/491; 562/16
[58] Field of Search ................ 562/15, 16; 548/491

[56] References Cited

U.S. PATENT DOCUMENTS 3,359,266 12/1967 Maier et al. ................ 562/16
4,100,275 7/1978 Ratcliffe et al. .

FOREIGN PATENT DOCUMENTS 0230266 7/1987 European Pat. Off. .
0309766 4/1989 European Pat. Off. .
WO90/09191 8/1990 WIPO .

OTHER PUBLICATIONS

Maier, et al., Phosphorous Sulfur, 8(1) 67–71 1980.
Jasny, et al., Science 260 1253–93 1993.
Talal, et al., Immunology Today, 4(7) 180–85 1983.
Habeshaw, et al., Immunology Today, 13(6) 207–10 1992.
Phosphous Sulfur (1980),8(1), 67–71 [Chem. Abstract 93:132560n].
Jasny, et al., "AIDS The Unanswered Questions", Science 260, (1993), 1253–1293.
Talal, et al., "A Clinician and a Scientist Look at Aquired Immune–Deficiency Syndrome (AIDS)", Immunology Today, 4(7), (1983), 180–185.
Habeshaw, et al., "Does the HIV Envolope Induce a Chronic Graft–Virus–Host–Like Disease?", Immunology Today, 13(6), (1992), 207–10.
Maier, Phosphorus and Sulfur, vol. 14, pp. 295–322 (1983).
Bartlett et al., Journal of American Chemical Society, vol. 106, pp. 4282–4283 (1984).
Katoh et al., Nature, vol. 329, pp. 654–656 (Oct. 15, 1987).
Billich et al., The J. of Biological Chem., vol. 263, No. 34, pp. 17905–17908 (Dec. 5, 1988).
Moore et al., Biochemical and Biophysical Res. Communications, vol. 159, No. 2, pp. 420–425 (Mar. 15, 1989).
Richards et al., FEBS Letters vol. 247, No. 1, pp. 113–117 (Apr. 1989).
von der Helm et al., FEBS Letters, vol. 247, No. 2, pp. 349–352 (Apr. 1989).
Meindl et al., Chemical Abstracts, vol. 78, 30152d, p. 540 (1973).
Rehse et al., Chemical Abstracts, vol. 108, 74899v, p. 633 (1988).
Pechik et al., FEBS Letters, vol. 247, No. 1, pp. 118–122 (Apr. 1989).

*Primary Examiner*—Joseph Conrad
*Attorney, Agent, or Firm*—Finnegan, Henderson, Farabow, Garrett & Dunner, L.L.P.

[57] ABSTRACT

The present invention relates to compounds of the formula I

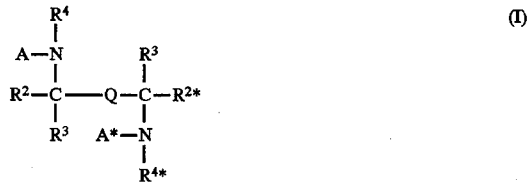

in which A, Q, $R^2$, $R^3$, $R^4$ and the corresponding radicals with an * are defined as indicated in the description, a process for the preparation thereof, and the use thereof for inhibiting retroviral proteases.

2 Claims, No Drawings

INHIBITORS OF RETROVIRAL PROTEASES

This application is a continuation of prior application Ser. No. 08/293,112 filed Aug. 19, 1994, now abandoned, which is a continuation of application Ser. No. 08/167,613 filed Dec. 16, 1993, abandoned, which is a continuation of application Ser. No. 07/627,818 filed Dec. 14, 1990, abandoned.

The present invention relates to substances which inhibit the action of retroviral proteases, processes for the preparation thereof, the use thereof and pharmaceuticals containing these.

The etiological case of "acquired immune deficiency syndrome" (AIDS) is the so-called human immunodeficiency virus (HIV) (F. Barre-Sinoussi et al., Science 220, (1983), 868–870; R. C. Gallo et al., Science 224, (1984), 500–502; R. C. Gallo and L. Montagnier, Scient. Am. 259(4), (1988), 40–48). HIV is a retrovirus and is a member of the group of lentiviruses (M. A. Gonda, F. Wong-Staal and R. C. Gallo, Science, 227, (1985), 173; P. Sonigo et al., Cell, 42, (1985), 369).

The AIDS epidemic has now spread to virtually all countries to a greater or lesser extent. To date about 160,000 cases of the disease have been reported from 149 countries to the World Health Organization (WHO). The WHO estimates the real number at about 500,000 cases, and the number of infected people at 5–10 millions (J. M. Mann at the 5th International Conference on AIDS, Montreal, June 4–9, 1989; see, for example, C&EN, Jun. 26, (1989), 7–16).

The only substance hitherto approved for the AIDS indication, zidovudine (AZT), is able in many cases to prolong the life of the patients but has serious, toxic side effects which force discontinuation of the therapy in many cases. Moreover, the first HIV strains which have shown a distinctly reduced sensitivity to AZT, and thus indicate the risk of resistance, have already been discovered (C&EN see above). Thus, further approaches to HIV therapy are urgently needed.

HIV proteins are, in analogy to proteins of other retroviruses, initially translated as long precursor gag, pol and env polyproteins (C. Dickson et al. in RNA Tumor Viruses (editors: R. Weiss, N. Teich, H. Varmus and J. Coffin), 2nd ed., revised, pages 513–648, Cold Spring Harbor Laboratory, Cold Spring Harbor, N.Y.) and are only subsequently processed by proteolysis to give the structural proteins (p 17 (MA), p24 (CA), p7 (NC) and p6), the enzymes (protease (PR), reverse transcriptase (RT) and integrase (IN)) and the coat proteins (gp120 (SU) and gp41 (TM)) (nomenclature: J. Leis et al., J. Virol, 62, (1988), (1808–1809). It is assumed that cleavage of the gag and pol polyproteins is brought about by a virally encoded protease. Mutations within the region encoding the protease lead to non-infectious virus particles (N. E. Kohl et al. Proc. Natl. Acad. Sci. USA 85, (1988), 4686–4690).

HIV protease is composed of 99 amino acids and evidently undergoes serf-elimination out of the pol polyprotein by hydrolysis of the two Phe-Pro linkages in positions 68–69 and 167–168 (M. C. Graves, J. J. Lim, E. P. Heimer and R. A. Kramer Proc. Natl. Acad. Sci. USA 85 (1988), 2449–2453; J. Hansen, S. Büilich, T. Schulze, S. Sukrow and K. Mölling, EMBO J. 7 (1988), 1785–1791; E. P. Lillehoj et al., J. Virology 62 (1988) 3053–3058; J. Schneider and S. B. H. Kent, Cell 54 (1988) 363–368).

Only a few inhibitors of HIV protease have been disclosed in the literature to date. The first representative was pepstatin A with an $IC_{50}$ of about 0.5 mmol (I. Katoh, T. Yasunaga, Y. Ikawa and Y. Yoshinaka, Nature, 329, (1987), 654–656). Since then, a few other inhibitors with moderate to good activity have been described (S. Billich et al., J. Biol. Chem. 34, (1988), 17905–17098; M. Moore et al., Biochem. Biophys. Res. Comm., 159, (1989), 420–425; A. D. Richards, R. Roberts, B. M. Dunn, M. C. Graves and J. Kay, FEBS Lett., 247, (1989), 113–117).

High doses of pepstatin A were able to bring about in the biosynthesis a reduction in the formation of the nuclear protein p24 and the activity of reverse transcriptase (K. v. d. Helm, L. Gürtler, J. Eberle and F. Deinhardt, FEBS Lett., 247, (1989), 349–352).

A new structural class which very effectively inhibits HIV protease in the enzyme assay has now been found.

The present invention relates to compounds of the formula I

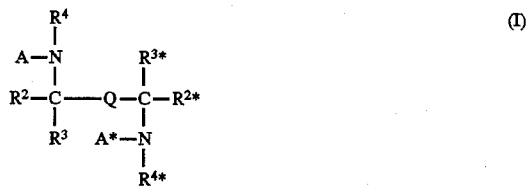

in which

Q is a radical of the formula IIa, IIb or IIc

Y is oxygen or sulfur and m is 0, 1 or 2;

A is a radical of the formula IV and A* is a radical of the formula IV*

where

E, E*, F, F*, G and G* are each, independently of one another, a natural or unnatural amino acid, aza amino acid or imino acid;

n, n*, o, o*, p and p* are each, independently of one another, 0 or 1;

D is $R^1$ or a radical of the formulae V, VI or VII and

D is $R^{1*}$ or a radical of the formulae V*, VI* or VII*,

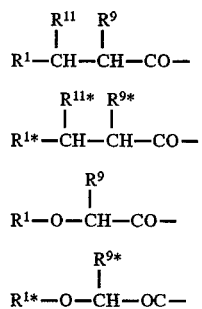

$$R^1-\underset{\underset{R^{11}}{|}}{CH}-\underset{\underset{R^9}{|}}{CH}-CO- \quad (VI)$$

$$R^{1*}-\underset{\underset{R^{11*}}{|}}{CH}-\underset{\underset{R^{9*}}{|}}{CH}-CO- \quad (VI^*)$$

$$R^1-O-\underset{\underset{R^9}{|}}{CH}-CO- \quad (VII)$$

$$R^{1*}-O-\underset{\underset{R^{9*}}{|}}{CH}-OC- \quad (VII^*)$$

and in which $R^1$ and $R^{1*}$ are each, independently of one another, $a_1$)
  hydrogen,
  carboxyl,
  $(C_1-C_{18})$-alkyl, which is optionally singly or doubly unsaturated and is optionally substituted by up to 3 identical or different radicals from the series comprising
    mercapto,
    hydroxyl,
    $(C_1-C_7)$-alkoxy,
    carbamoyl,
    $(C_1-C_8)$-alkanoyloxy,
    carboxyl,
    $(C_1-C_7)$-alkoxycarbonyl,
    F, Cl, Br, I,
    amino,
    amidino which can optionally be substituted by one, two or three $(C_1-C_8)$-alkyl radicals.
    guanidino which can optionally be substituted by one or two benzyloxycarbonyl radicals or by one, two, three or four $(C_1-C_8)$-alkyl radicals,
    $(C_1-C_7)$-alkylamino,
    di- $(C_1-C_7)$-alkylamino,
    $(C_1-C_8)$-alkoxycarbonylamino,
    $(C_7-C_{15})$-aralkoxycarbonyl,
    $(C_7-C_{15})$-aralkoxycarbonylamino,
    phenyl-$(C_1-C_4)$-alkoxy,
    9-fluorenylmethoxycarbonylamino,
    $(C_1-C_6)$-alkylsulfonyl,
    $(C_1-C_6)$-alkylsulfinyl,
    $(C_1-C_6)$-alkylthio,
    hydroxamino,
    hydroximino,
    sulfamoyl,
    sulfo,
    carboxamido,
    formyl,
    hydrazono,
    imino,
    a radical $CONR^{12}R^{13}$ or $CONR^{12*}R^{13*}$,
    by up to three phenyl,
    by up to six hydroxyl or
    by up to five $(C_1-C_8)$-alkanoyloxy;
  mono-, bi- or tricyclic $(C_3-C_{18})$-cycloalkyl,
  $(C_3-C_{18})$-cycloalkyl-$(C_1-C_6)$-alkyl, where the cycloalkyl moiety is in each case optionally substituted by one or two identical or different radicals from the series comprising
    F, Cl, Br, I,
    carboxyl,
    carbamoyl,
    carboxymethoxy,
    hydroxyl,
    $(C_1-C_7)$-alkoxy,
    $(C_1-C_7)$-alkyl,
    $(C_1-C_7)$-alkyloxycarbonyl,
    amino,
    $(C_1-C_6)$-alkylamino-$(C_1-C_6)$-alkyl,
    di-$(C_1-C_6)$-alkylamino-$(C_1-C_6)$-alkyl,
    amidino,
    hydroxamino,
    hydroximino,
    hydrazono,
    imino,
    guanidino,
    $(C_1-C_6)$-alkoxysulfonyl,
    $(C_1-C_6)$-alkoxysulfinyl,
    $(C_1-C_6)$-alkoxycarbonylamino,
    $(C_6-C_{12})$-aryl-$(C_1-C_4)$-alkoxycarbonylamino,
    $(C_1C_7)$-alkylamino,
    di-$(C_1C_7)$-alkylamino and
    trifluoromethyl;
  $(C_6-C_{14})$-aryl,
  $(C_6-C_{14})$-aryl-$(C_1-C_6)$-alkyl or
  $(C_6-C_{14})$-aryl-$(C_3-C_8)$-cycloalkyl, in which the aryl moiety is in each case optionally substituted by one, two or three identical or different radicals from the series comprising
    F, Cl, Br, I,
    hydroxyl,
    mono-, di- or trihydroxy-$(C_1-C_4)$-alkyl,
    trifluoromethyl,
    formyl,
    carboxamido,
    mono- or di-$(C_1-C_4)$-alkylaminocarbonyl,
    nitro,
    $(C_1-C_7)$-alkoxy,
    $(C_1-C_7)$-alkyl,
    $(C_1-C_7)$-alkoxycarbonyl,
    amino,
    $(C_1-C_7)$-alkylamino,
    di-$(C_1-C_7)$-alkylamino,
    carboxyl,
    carboxymethoxy,
    amino-$(C_1-C_7)$-alkyl,
    $(C_1-C_7)$-alkylamino-$(C_1-C_7)$-alkyl,
    di-$(C_1-C_7)$-alkylamino-$(C_1-C_7)$-alkyl,
    $(C_1-C_7)$-alkoxycarbonylmethoxy,
    carbamoyl,
    sulfamoyl,
    $(C_1-C_7)$-alkoxysulfonyl,
    $(C_1-C_8)$-alkylsulfonyl,
    sulfo-$(C_1-C_8)$-alkyl,
    guanidino-$(C_1-C_8)$-alkyl and
    $(C_1-C_6)$ -alkoxycarbonylamino;
  Het,
  Het-$(C_1-C_6)$-alkyl,
  Het-$(C_3-C_8)$-cycloalkyl,
  Het-$(C_3-C_8)$-cycloalkyl-$(C_1-C_4)$-alkyl,
  Het-$(C_3-C_8)$-cycloalkoxy-$(C_1-C_4)$-alkyl,
  Het-thio-$(C_1-C_6)$-alkyl,
  Het-thio-$(C_3-C_8)$-cycloalkyl,
  Het-thio-$(C_3-C_8)$-cycloalkyl-$(C_1-C_4)$-alkyl, where Het is in each case the radical of a 5- to 7-membered monocyclic or 8- to 10-membered bicyclic ring system which can be benzo-fused, aromatic, partially hydrogenated or completely hydrogenated, which can contain as hetero elements one, two, three or four different radicals from the group comprising N, O, S, NO, SO, $SO_2$, which can be substituted by 1 to 6 hydroxyl and which is optionally mono-, di- or trisubstituted as defined for ($C_6$–$C_{14}$)-aryl under $a_1$) and/or by oxo, or a radical $NR^{12}R^{13}$ or $NR^{12*}R^{13*}$ or $a_2$)
a radical of the formula VIII or VIII*

$$R^{1a}—W \quad \text{(VIII)}$$

$$R^{1a*}—W* \quad \text{(VIII*)}$$

in which $R^{1a}$ and $R^{1a*}$ are defined as $R^1$ and $R^{1*}$, respectively, under $a_1$), and W or W* is —CO—, —CS—, —O—CO—, —$SO_2$—, —SO—, —S—, —$NHSO_2$—, —NHCO—, —CH(OH)—, —N(OH)— or —CO—V— where V is a peptide with 1 to 10 amino acids;

or in which $R^1$ and $R^{1*}$ form, independently of one another, together with $R^{11}$ and $R^{11*}$, respectively, and with the atoms carrying them, mono- or bicyclic, saturated or partially unsaturated ring systems which have 5–12 ring members and which, apart from carbon, can also contain 1 sulfur atom which can optionally be oxidized to the sulfoxide or sulfone;

$a_3$)
a glycosyl radical, preferably a glucofuranosyl or glucopyranosyl radical, which is derived from naturally occurring aldotetroses, aldopentoses, aldohexoses, ketopentoses, ketohexoses, deoxyaldoses, aminoaldoses and oligosaccharides and the stereoisomers thereof;

$R^2$ and $R^{2*}$ are, independently of one another, defined as $R^1$ and $R^{1*}$, respectively under $a_1$,) or $a_2$) or form, together with $R^4$ and $R^{4*}$, respectively, and the atoms carrying them, mono- or bicyclic, saturated or partially unsaturated ring systems with 5 to 12 ring members, or form, together with $R^3$ and $R^{3*}$, respectively, and the atoms carrying them, cyclic, saturated or partially unsaturated ring systems with 3 to 12 ring members;

$R^3$ and $R^{3*}$ are each, independently of one another
hydrogen or
($C_1$–$C_3$)-alkyl;

$R^4$ and $R^{4*}$ are each, independently of one another,
hydrogen or
($C_1$–$C_8$)-alkyl;

$R^5$ is
hydrogen,
($C_1$–$C_{20}$)-alkyl,
($C_2$–$C_{20}$)-alkenyl or alkynyl,
($C_7$–$C_{20}$)-arylalkyl, ($C_6$–$C_{20}$)-aryl,
($C_3$–$C_8$)-cycloalkyl, each of which can optionally be substituted by various radicals from the series comprising hydroxyl, alkoxy, carboxyl, alkanoyloxy, alkoxycarbonyl, F, Cl, Br, l, amino, alkylamino or dialkylamino;
an equivalent of a pharmaceutically tolerated cation, or
a phosphate prodrug;

$R^6$ is oxygen or sulfur;
$R^7$ and $R^{7*}$ are each, independently of one another,
hydrogen,
($C_1$–$C_{20}$)-alkyl,
($C_2$–$C_{20}$)-alkenyl or alkynyl, ($C_1$–$C_{20}$)-aryl, ($C_7$–$C_{20}$)-arylalkyl, each of which can optionally be substituted by various radicals from the series comprising hydroxyl, alkoxy, carboxyl, alkanoyloxy, alkoxycarbonyl, F, Cl, Br, l, amino, alkylamino, dialkylamino,
or can together form a ring with 2–6 carbon atoms;

$R^8$ and $R^{8*}$ are each, independently of one another,
hydrogen or
($C_1$–$C_8$)-alkyl,
or form, together with $R^9$ and $R^{9*}$, respectively, and the atoms carrying them, mono- or bicyclic, saturated or partially unsaturated ring systems with 5–12 ring members;

$R^9$ and $R^{9*}$, each, independently of one another, defined as $R^1$ and $R^{1*}$, respectively, under $a_1$), are each hydroxyl or ($C_1$–$C_4$)-alkanoyloxy or form, together with $R^{10}$ and $R^{10*}$, respectively, and the atoms carrying them, cyclic, saturated or partially unsaturated ring systems with 3 to 12 ring members; or form, together with $R^{11}$ and $R^{11*}$, respectively, and the atoms carrying them, a mono- or bicyclic, saturated or partially unsaturated ring system which has 5–12 ring members and, apart from carbon, can also contain 1 sulfur atom which can optionally be oxidized to the sulfoxide or sulfone; or can contain 1 nitrogen atom, it being possible for the ring system to be optionally substituted by amino;

$R^{10}$ and $R^{10*}$ are each, independently of one another,
hydrogen or
($C_1$–$C_6$)-alkyl;

$R^{11}$ and $R^{11*}$ are each, independently of one another,
hydrogen,
hydroxyl,
($C_1$–$C_4$)-alkanoyloxy or
($C_1$–$C_8$)-alkyl;

$R^{12}$, $R^{12*}$, $R^{13}$ and $R^{13*}$ are each, independently of one another,
hydrogen,
($C_1$–$C_8$)-alkyl which can be substituted by
amino,
($C_1$–$C_4$)-alkylamino,
di-($C_1$–$C_4$)-alkylamino,
mercapto,
carboxyl,
hydroxyl or
($C_1$–$C_4$)-alkoxy, or
($C_3$–$C_7$)-cycloalkyl,
($C_1$–$C_4$)-alkoxycarbonyl,
($C_6$–$C_{14}$)-aryl, ($C_6$–$C_{14}$)-aryl-($C_1$–$C_4$)-alkoxycarbonyl, each of which can be substituted in the aryl moiety as described for $R^1$ and $R^{1*}$,
Het or
Het-($C_1$–$C_4$)-alkyl, where Het is defined as described for $R^1$ and $R^{1*}$,
or where $R^{12}$ and $R^{13}$ or $R^{12*}$ and $R^{13*}$ form, together with the nitrogen atoms carrying them, monocyclic or bicyclic, saturated, partially unsaturated or aromatic ring systems which can contain, as further ring members besides carbon, also 1 or 2 nitrogen atoms, 1 sulfur atom or 1 oxygen atom, and be substituted by ($C_1$–$C_4$)-alkyl, where one or more amide groups (—CONH—) in the main chain in the abovementioned compounds of the formula I can be replaced by —$CH_2NR^{14}$—, —$CH_2S$—, —$CH_2O$—, —$OCH_2$—, —$CH_2CH_2$—, —CH=CH— (cis and trans), —$COCH_2$—, —CH (OH)CH$_2$—, —CH$_2$SO—, —CH$_2$—, —COO—, —P(O)(OR$^{15}$)CH$_2$— and —P(O)(OR$^{15}$)NH—, or else by an amide group of reverse polarity (—NHCO—);

in which R$^{14}$ and R$^{15}$ are each, independently of one another, hydrogen or (C$_1$–C$_4$)-alkyl;

and the physiologically tolerated salts thereof.

The nomenclature used in this description follows the general practice for amino acids, that is to say the amino group is on the left and the carboxyl group is on the right of each amino acid. A corresponding statement applies to aza amino acids and imino acids.

Those natural or unnatural amino acids which are chiral can be in the D or L form. Ó-Amino acids are preferred. The following examples may be mentioned:

Aad, Abu, γAbu, ABz, 2ABz, εAca, Ach, Acp, Adpd, Ahb, Aib, βAib, βAla, ΔAla, Ala, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guv, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Iva, Kyn, Lant, Lcn, Leu, Lsg, Lys, βLys, ΔLys, Met, Mira, Min, nArg, Nle, Nva, Oly, Orn, Pan, Pec, Pen, Phe, Phg, Pic, Pro, ΔPro, Pse, Pya, Pyr, Pza, Qin, Ros, Sar, Sec, Sero, Ser, Thi, βThi, Thr, Thy, Thx, Tia, TIe, Tly, Trp, Trta, Tyr, Val, Nal, Tbg, Npg, Chg, Thia, (cf., for example, Houben-Weyl, Methoden der organischen Chemie (Methods of Organic Chemistry), volume XV/1 and 2, Stuttgart, 1974):

Aza amino acids are natural or unnatural amino acids where the central —CHR— or —CH$_2$— unit has been replaced by —NR— or —NH—.

An imino acid means in general natural or unnatural amino acids whose amino group is monosubstituted. Particular mention may be made in this connection of compounds substituted by (C$_1$–C$_8$)-alkyl which in turn is optionally substituted as described on page 4. Also suitable are heterocycles from the following group:

Pyrrolidine-2-carboxylic acid; piperidine-2-carboxylic acid;

1,2,3,4-tetrahydroisoquinoline-3-carboxylic acid;

decahydroisoquinoline-3-carboxylic acid;

octahydroindole-2-carboxylic acid;

decahydroquinoline-2-carboxylic acid;

octahydrocyclopenta[b]pyrrole-2-carboxylic acid;

2-azabicyclo[2.2.2]octane-3-carboxylic acid;

2-azabicyclo[2.2.1]heptane-3-carboxylic acid;

2-azabicyclo[3.1.0]hexane-3-carboxylic acid;

2-azaspiro[4.4]nonane-3-carboxylic acid;

2-azaspiro[4.5]decane-3-carboxylic acid;

spiro[(bicyclo[2.2.1]-heptane)-2,3-pyrrolidine-5-carboxylic acid];

spiro[(bicyclo[2.2.2]octane)-2,3-pyrrolidine-5-carboxylic acid];

2-azatricyclo[4.3.0.1$^{6,9}$]decane-3-carboxylic acid;

decahydrocyclohepta[b]pyrrole-2-carboxylic acid;

decahydrocycloocta[b]pyrrole-2-carboxylic acid;

octahydrocyclopenta[c]pyrrole-2-carboxylic acid;

octahydroisoindole-1-carboxylic acid;

2,3,3a,4,6a-hexahydrocyclopenta[b]pyrrole-2-carboxylic acid;

2,3,3a,4,5,7a-hexahydroindole-2-carboxylic acid;

tetrahydrothiazole-4-carboxylic acid;

isoxazolidine-3-carboxylic acid; pyrazolidine-3-carboxylic acid;

hydroxyproline-2-carboxylic acid; all of which can optionally be substituted:

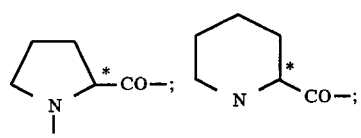

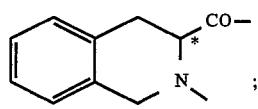

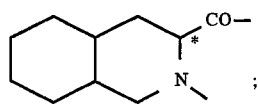

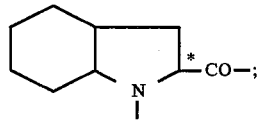

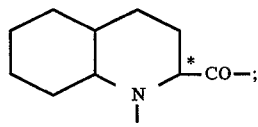

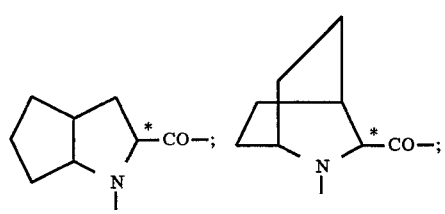

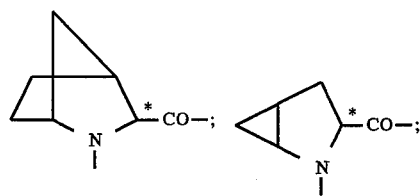

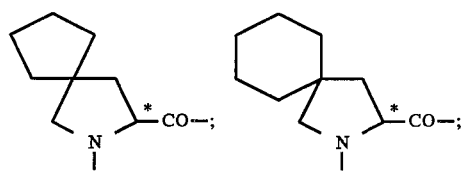

-continued

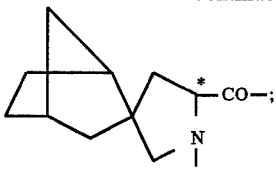

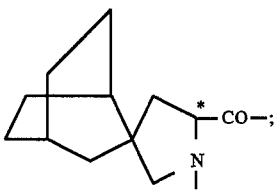

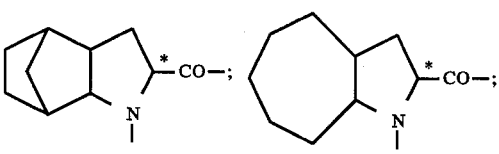

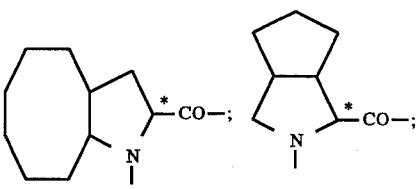

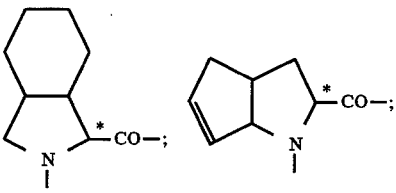

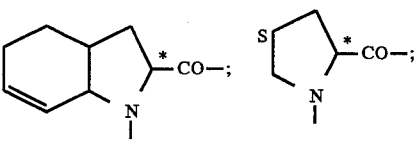

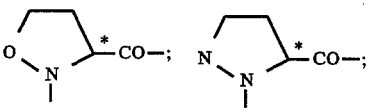

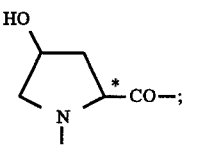

Glycosyl radicals as described above are derived, in particular, from natural D- or L-monosaccharides occurring in microorganisms, plants, animals or humans, such as ribose (Rib), arabinose (Ara), xylose (Xyl), lyxose (Lyx), aliose (All), altrose (Alt), glucose (Glc), mannose (Man), gulose (Gul), idose (Ido), galactose (Gal), talose (Tal), erythrose (Ery), threose (Thr), psicose (Psi), fructose (Fru), sorbose (Sor), tagatose (Tag), xylulose (Xyu), fucose (Fuc), rhamnose (Rha), olivose (Oli), oliose (Olo), mycarose (Myc), rhodosamine (RN), N-acetylglucosamine (GlcNAc), N-acetylgalactosamine (GalNAc), N-acetylmannosamine (ManNAc) or disaccharides such as maltose (Mal), lactose (Lac); cellobiose (Cel), gentibiose (Gen), N-acetyllactosamine (LacNAc), chitobiose (Chit), β-galactopyranosyl-(1–3)-N-acetylgalactosamine and β-galactopyranosyl-(1–3)- or -(1–4)-N-acetylglucosamine, and their synthetic derivatives such as 2-deoxy-, 2-amino-, 2-acetamido- or 2-halogeno-, preferably bromo- and iodo-sugars.

The centers of chirality in the compounds of the formula (I) can have the R or S or R,S configuration.

Alkyl can be straight-chain or branched. A corresponding statement applies to radicals derived therefrom, such as, for example, alkoxy, alkylthio, alkylamino, dialkylamino, alkanoyl and aralkyl.

Cycloalkyl also means alkyl-substituted radicals such as, for example, 4-methylcyclohexyl or 2,3-dimethylcyclopentyl.

Bicycloalkyl or tricycloalkyl means an isocyclic aliphatic, non-aromatic radical which can optionally contain unsymmetrically distributed double bonds and can optionally also be substituted by non-cyclic aliphatic side chains. The two or three rings of which a radical of this type is composed are fused or spiro-linked and linked via a ring carbon atom or a side-chain carbon atom. Examples of these radicals are bornyl, norbornyl, pinanyl, norpinanyl, caranyl, norcaranyl, thujanyl, adamantyl, bicyclo[3.3.0]octyl, bicyclo[4.4.0]decyl, bicyclo[1.1.0]butyl, spiro[3.3]heptyl substituents.

If the said cyclic elements carry more than one substituent, these can be both cis and trans with respect to one another.

$(C_6-C_{14})$-Aryl is, for example, phenyl, naphthyl, biphenylyl or fluorenyl; phenyl and naphthyl are preferred. A corresponding statement applies to radicals derived therefrom, such as, for example, aryloxy, aroyl, aralkyl and aralkoxy. Aralkyl means an unsubstituted or substituted $(C_6-C_{14})$-aryl radical linked to $(C_1-C_6)$-alkyl, such as, for example, benzyl, 1- and 2-naphthylmethyl, but without aralkyl being restricted to the said radicals.

Het radicals within the meaning of the abovementioned definition are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindolyl, indazolyl, phthalazinyl, quinolyl, isoquinolyl, quinoxalinyl, quinazolinyl, cinnolinyl, β-carbolinyl or a benzo-fused cyclopenta- cyclohexa- or cycloheptafused derivative of these radicals.

These heterocycles can be substituted on one nitrogen atom by oxides; $(C_1-C_7)$-alkyl, for example methyl or ethyl; phenyl; phenyl-$(C_1-C_4)$-alkyl, for example benzyl; and/or on one or more carbon atoms by $(C_1-C_4)$-alkyl, for example methyl; phenyl; phenyl-$(C_1-C_4)$-alkyl, for example benzyl; halogen; hydroxyl; $(C_1-C_4)$-alkoxy, for example methoxy, phenyl-$(C_1-C_{14})$-alkoxy, for example benzyloxy, or oxo, and be partially or completely saturated.

Examples of such radicals are 2- or 3-pyrrolyl; phenylpyrrolyl, for example 4- or 5-phenyl-2-pyrrolyl; 2-furyl; 2-thienyl; 4-imidazolyl; methylimidazolyl, for example 1-methyl-2-, 4- or 5-imidazolyl; 1,3-thiazol-2-yl; 2-, 3- or 4-pyridyl; 2-, 3- or 4-pyridyl 1-oxide; 2-pyrazinyl; 2-, 4- or 5-pyrimidinyl; 2-, 3- or 5-indolyl; substituted 2-indolyl, for example 1-methyl-, 5-methyl-, 5-methoxy-, 5-benzyloxy-, 5-chloro- or 4,5-dimethyl-2-indolyl; 1-benzyl-2- or 3-indolyl; 4,5,6,7-tetrahydro-2-indolyl; cyclohepta[b]-5-pyrrolyl; 2-, 3- or 4-quinolyl; 1-, 3- or 4-isoquinolyl; 1-oxo-1,2-dihydro-3-isoquinolyl;

2-quinoxalinyl; 2-benzofuranyl; 2-benzoxazolyl; benzothiazolyl; benzo[e]indol-2-yl or β-carbolin-3-yl.

Examples of partially hydrogenated or completely hydrogenated heterocyclic rings are dihydropyridinyl; pyrrolidinyl, for example 2-, 3- or 4-N-methylpyrrolidinyl; poperazinyl; morpholino; thiomorpholino; tetrahydrothienyl, benzodioxolanyl.

Halogen is fluorine, chlorine, bromine or iodine, especially fluorine or chlorine.

Salts of the compounds of the formula (I) means, in particular, pharmaceutically utilizable or non-toxic salts.

Salts of this type are formed, for example, by compounds of the formula (I) which contain acid groups, for example carboxyl, with alkali metals or alkaline earth metals, such as, for example Na, K, Mg and Ca, and with physiologically tolerated organic amines such as, for example, triethylamine and tris(2-hydroxyethyl)amine.

Compounds of the formula (I) which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Phosphate prodrugs are described, for example, in H. Bundgaard, "Design of Prodrugs", Elsevier, Amsterdam 1985, pages 70 et seq. Examples of such prodrug forms are glyceryl esters, 1,2-difatty acid glyceryl triesters, O-acyloxyalkyl esters and 1-methyl-2-nitroethyl esters.

Preferred pharmaceutically tolerated cations are sodium, potassium, magnesium, aluminum, lithium, ammonium and triethylammonium.

Preferred compounds of the formula I are those in which the radicals and symbols with and without the asterisk are identical in each case.

Particularly preferred compounds of the formula I are furthermore those in which Q is a radical of the formulae IIa or IIb;
Y is oxygen or sulfur;
A, A*, D, D*, n, n*, o, o*, p and p* are as defined above;
E, E*, F, F*, G and G* are each, independently of one another, a natural or unnatural α-amino acid or α-imino acid;
$R^1$ and $R^{1*}$ are each, independently of one another,
$a_1$)
  hydrogen;
  carboxyl;
  $(C_1-C_{12})$-alkyl, which is optionally singly unsaturated and is optionally substituted by up to 2 identical or different radicals from the series comprising
    hydroxyl,
    $(C_1-C_4)$-alkoxy,
    carbamoyl,
    $(C_1-C_8)$-alkanoyloxy,
    carboxyl,
    $(C_1-C_4)$-alkoxycarbonyl,
    F,
    amino,
    $(C_1-C_7)$-alkylamino,
    di-$(C_1-C_7)$-alkylamino,
    $(C_1-C_6)$-alkoxycarbonylamino,
    benzyloxycarbonyl,
    benzyloxycarbonylamino,
    9-fluorenylmethoxycarbonylamino,
    $(C_1-C_4)$-alkylsulfonyl,
    a radical $CONR^{12}R^{13}$ or $CONR^{12*}R^{13*}$,
    by up to three phenyl,
    by up to six hydroxyl or
    by up to four $(C_1-C_8)$-alkanoyloxy; or
  mono- or bicyclic $(C_3-C_{12})$-cycloalkyl,
  $(C_3-C_{12})$-cycloalkyl-$(C_1-C_6)$-alkyl, where the cycloalkyl moiety is in each case optionally substituted by one or two identical or different radicals from the series comprising
    F,
    carboxyl,
    hydroxyl,
    $(C_1-C_7)$-alkoxy,
    $(C_1-C_4)$-alkyl,
    $(C_1-C_4)$-alkoxycarbonyl,
    amino,
    $(C_1-C_6)$-alkoxycarbonylamino,
    benzyloxycarbonylamino,
    $(C_1-C_4)$-alkylamino and
    di-$(C_1-C_4)$-alkylamino; or
  $(C_6-C_{10})$-aryl,
  $(C_6-C_{10})$-aryl-$(C_1-C_6)$-alkyl, in which the aryl moiety is in each case optionally substituted by one, two or three identical or different radicals from the series comprising
    F, Cl, Br,
    hydroxyl,
    hydroxy-$(C_1-C_4)$-alkyl,
    carboxamido,
    mono- or di-$(C_1-C_4)$-alkylaminocarbonyl,
    $(C_1-C_4)$-alkoxy,
    $(C_1-C_4)$-alkyl,
    $(C_1-C_4)$-alkoxycarbonyl,
    amino,
    $(C_1-C_4)$-alkylamino,
    di-$(C_1-C_4)$-alkylamino,
    carboxyl,
    carbamoyl,
    $(C_1-C_4)$-alkoxycarbonylamino; or
  Het,
  Het-$(C_1-C_6)$-alkyl,
  Het-$(C_5-C_6)$-cycloalkyl,
  Het-thio-$(C_1-C_4)$-alkyl,
  Het-thio-$(C_5-C_6)$-cycloalkyl, where Het is in each case the radical of a 5- to 6-membered monocyclic or 8- to 10-membered bicyclic ring system which can be aromatic, partially hydrogenated or completely hydrogenated, which can contain as hetero elements one, two, three or four different radicals from the group comprising N, O, S, NO, SO, $SO_2$, which can be substituted by 1 to 4 hydroxyl, and which is optionally mono- or disubstituted as defined for $(C_6-C_{10})$-aryl under $a_1$),
  or a radical $NR^{12}R^{13}$ or $NR^{12*}R^{13*}$, or
$a_2$)
  a radical of the formula VIII or VIII*

$$R^{1a}—W \qquad (VIII)$$

$$R^{1a*}—W* \qquad (VIII*)$$

in which $R^{1a}$ and $R^{1a*}$ are defined as $R^1$ and $R^{1*}$, respectively, under $a_1$), and W and W* are each —CO—, —O—CO—, —$SO_2$—, —SO—, —S—, —NHCO— or —CH(OH)—;

or in which $R^1$ add $R^{1*}$ form, independently of one another, together with $R^{11}$ and $R^{11*}$, respectively, and the atoms carrying them, monocyclic, saturated or partially unsaturated ring systems which have 5–8 ring members which, apart from carbon, can also contain 1 sulfur atom which can optionally be oxidized to the sulfoxide or sulfone;

$a_3$)

a glycosyl radical which is as defined above;

$R^2$ and $R^{2*}$ are each, independently of one another, $b_1$)

hydrogen, carboxyl, $(C_1-C_{10})$-alkyl which is optionally singly or doubly unsaturated and which is optionally substituted by up to 3 identical or different radicals from the series comprising hydroxyl, $(C_1-C_7)$-alkoxy, $(C_1-C_7)$-alkylthio, $(C_1-C_7)$-alkylsulfinyl, $(C_1-C_7)$-alkylsulfonyl, $(C_1-C_7)$-alkanoyloxy, carboxyl, $(C_1-C_7)$-alkoxycarbonyl, Cl, Br, amino, amidino, guanidino, N,N'-di-(benzyloxycarbonyl)-guanidino, carbamoyl, $(C_7-C_{15})$-aralkoxycarbonyl, $(C_1-C_5)$-alkoxycarbonylamino, $(C_7-C_{15})$-aralkoxycarbonylamino or 9-fluorenylmethoxycarbonylamino; or $(C_3-C_{12})$-cycloalkyl, $(C_3-C_{12})$-cycloalkyl-$(C_1-C_3)$-alkyl, $(C_6-C_{14})$-aryl, $(C_6-C_{14})$-aryl-$(C_1-C_3)$-alkyl, where the aryl moiety is in each case optionally substituted by one, two or three identical or different radicals from the series comprising F, Cl, Br, I, hydroxyl, $(C_1-C_7)$-alkoxy, $(C_1-C_7)$-alkyl, $(C_1-C_7)$-alkoxycarbonyl, amino and trifluoromethyl; or Het-$(C_1-C_6)$-alkyl, where Het is the radical of a 5- or 6-membered monocyclic or 9- to 10-membered bicyclic, optionally partially or completely hydrogenated heteroaromatic compound which has at least one carbon atom, 1–4 nitrogen atoms and/or 1–2 sulfur atoms and/or 1–2 oxygen atoms as ring members and which is optionally mono- or disubstituted as described on pages 5/6 for the aryl moiety; or $b_2$)

form, together with $R^4$ and $R^{4*}$, respectively, and the atoms carrying them, pyrrolidine or piperidine, each of which can also be fused to cyclopentyl, cyclohexyl or phenyl, or form, together with $R^3$ and $R^{3*}$, respectively, and the atoms carrying them, cyclic, saturated or partially unsaturated ring systems with 3–8 ring members; $R^3$ and $R^{3*}$ are each, independently of one another, hydrogen, methyl or ethyl;

$R^4$ and $R^{4*}$ are each, independently of one another, hydrogen, $(C_1-C_4)$-alkyl;

$R^5$ is hydrogen, $(C_1-C_6)$-alkyl, $(C_2-C_6)$-alkenyl or alkynyl, $(C_7-C_{20})$-arylalkyl, $(C_6-C_{10})$-aryl, one equivalent of a pharmaceutically tolerated cation, or is glyceryl ester, 1,2-difatty acid glyceryl triester, O-acyloxyalkyl ester or 1-methyl-2-nitroethyl ester, $R^6$ is oxygen or sulfur; $R^7$ is defined as described on page 8, $R^8$ and $R^{8*}$ are each, independently of one another, hydrogen, $(C_1-C_8)$ or form, together with $R^9$ and $R^{9*}$, respectively, and the atoms carrying them, pyrrolidine or piperidine, each of which can additionally be fused to cyclopentyl, cyclohexyl or phenyl;

$R^9$ and $R^{9*}$ are each, independently of one another, defined as $R^2$ and $R^{2*}$, respectively, under $b_1$) or are $(C_1-C_8)$-alkanoyloxy or form, together with $R^{10}$ and $R^{10*}$, respectively, and the atoms carrying them, cyclic, saturated or partially unsaturated ring systems with 5 to 12 ring members; or form, together with $R^{11}$ and $R^{11*}$, respectively, and the atoms carrying them, a mono- or bicyclic, saturated or partially unsaturated ring system which has 5–12 ring members and which can, besides carbon, also contain 1 sulfur atom which can optionally be oxidized to the sulfoxide or sulfone;

$R^{10}$ and $R^{10*}$ are each, independently of one another, hydrogen or $(C_1-C_4)$-alkyl;

$R^{11}$ and $R^{11*}$ are each, independently of one another, hydrogen, hydroxyl, $(C_1-C_4)$-alkanoyloxy or $(C_1-C_4)$-alkyl;

$R^{12}$, $R^{12*}$, $R^{13}$ and $R^{13*}$ are each, independently of one another, hydrogen, $(C_1-C_8)$-alkyl which can be substituted by amino, $(C_1-C_4)$-alkylamino, di-$(C_1-C_4)$-alkylamino, carboxyl, hydroxyl or $(C_1-C_4)$-alkoxy, or $(C_1-C_4)$-alkoxycarbonyl, $(C_6-C_{10})$-aryl which can be substituted as described for $R^1$ and $R^{1*}$, $(C_6-C_{10})$-aryl-$(C_1-C_4)$-alkoxycarbonyl, Het or Het-$(C_1-C_4)$-alkyl, where Het is defined as described for $R^1$ and $R^{1*}$, where one or more amide groups (—CONH—) in the main chain in the abovementioned compounds of the formula I can be replaced by a group composed of —$CH_2NR^{14}$—, —CH$_2$O—, —OCH$_2$—, —CH$_2$CH$_2$—, —COCH$_2$—, —CH(OH)CH$_2$—, —COO— or else by an amide group of reverse polarity (—NHCO—);

R$^{14}$ is
hydrogen or
(C$_1$–C$_4$)-alkyl;

and the physiologically tolerated salts thereof.

Particularly preferred compounds of the formula I are those in which

Q is a radical of the formulae IIa or IIb;

Y, A, A*, D, D*, n, n*, o, o* are as defined above, p and p* are 1;

R$^1$ and R$^{1*}$ are each, independently of one another,
hydrogen,
carboxyl,
(C$_1$–C$_{10}$)-alkyl,
(C$_3$–C$_8$)-cycloalkyl,
(C$_3$–C$_8$)-cycloalkyl-(C$_1$–C$_{10}$)-alkyl,
phenyl-(C$_1$–C$_8$)-alkyl which can be substituted in the phenyl moiety as described on pages 17/18,
triphenyl-(C$_1$–C$_4$)-alkyl,
optionally protected mono- or di-amino-(C$_1$–C$_{10}$)-alkyl or amino-(C$_6$–C$_{10}$)-aryl-(C$_1$–C$_4$)-alkyl or amino-(C$_3$–C$_{10}$)-cycloalkyl-(C$_1$–C$_4$)-alkyl such as 2-amino-3-phenylpropyl,
mono-, di-, tri-, tetra-, penta- or hexahydroxy-(C$_1$–C$_{10}$)-alkyl or -alkanoyl,
(C$_1$–C$_4$)-alkoxy-(C$_1$–C$_{10}$)-alkyl,
(C$_1$–C$_4$)-alkoxycarbonyl-(C$_1$–C$_{10}$)-alkyl,
(C$_1$–C$_8$)-alkylsulfonyl,
(C$_1$–C$_8$)-alkylsulfinyl,
mono-, di-, trihydroxy-(C$_1$–C$_8$)-alkylsulfonyl,
mono-, di-, trihydroxy-(C$_1$–C$_8$)-alkylsulfinyl,
mono-, di-, tri- or tetra-(C$_1$–C$_8$)-alkanoyloxy-(C$_1$–C$_{10}$)-alkyl,
(C$_1$–C$_{11}$)-alkanoyl,
optionally protected amino-(C$_1$–C$_{11}$)-alkanoyl,
di-(C$_1$–C$_7$)-alkylamino-(C$_2$–C$_{11}$)-alkanoyl,
(C$_3$–C$_9$)-cycloalkylcarbonyl,
amino-substituted (C$_3$–C$_9$)-cycloalkylcarbonyl,
amino-substituted (C$_3$–C$_9$)-cycloalkylsulfonyl,
(C$_6$–C$_{10}$)-aryl-(C$_2$–C$_{11}$)-alkanoyl,
benzoyl, benzenesulfonyl or (C$_6$–C$_{10}$)-aryl-(C$_1$–C$_4$)-alkylcarbonyl or -sulfonyl, each of which is optionally substituted by amino, halogen, (C$_1$–C$_7$)-alkyl, (C$_1$–C$_7$)-alkoxy or (C$_1$–C$_7$)-alkoxycarbonyl, or
(C$_1$–C$_{10}$)-alkoxycarbonyl,
substituted (C$_1$–C$_{10}$)-alkoxycarbonyl such as
2-(trimethylsilyl)ethoxycarbonyl,
2,2,2-trichloroethoxycarbonyl or
1,1-dimethyl-2,2,2-trichloroethoxycarbonyl,
(C$_6$–C$_{10}$)-aryl-(C$_1$–C$_6$)-alkoxycarbonyl,
(C$_6$–C$_{10}$)-aryl-(C$_1$–C$_8$)-alkyl, (C$_3$–C$_{10}$)-cycloalkyl-(C$_1$–C$_8$)-alkyl or (C$_1$–C$_{10}$)-alkyl, each of which is substituted by optionally protected amino and hydroxyl, such as
2-amino-1-hydroxy-4-methylpentyl,
9-fluorenylmethoxycarbonyl,
ketohexosyl,
ketopentosyl,
deoxyhexoketosyl,
deoxypentoketosyl,
aldohexosyl,
aldopentosyl,
deoxyhexoaldosyl,
deoxypentoaldosyl,
2-amino-2-deoxyhexosyl,
2-acetamido-2-deoxyhexosyl,
lactosyl or
maltosyl, it being possible for the linked sugars to be in the pyranose or furanose form,
Het-(C$_1$–C$_6$)-alkyl,
Het-carbonyl or -sulfonyl,
Het-(C$_1$–C$_6$)-alkylcarbonyl or -sulfonyl,
Het-mercapto-(C$_1$–C$_6$)-alkylcarbonyl or -sulfonyl, where Het is in each case furyl, thienyl, pyrrolyl, imidazolyl, isoxazolyl, thiazolyl, pyrazolyl, triazolyl, pyridyl, pyrimidyl, pyrazinyl, pyridazinyl, triazinyl, pyrrolidyl, piperidyl, piperazinyl, morpholino, thiomorpholino, tetrahydrofuryl, tetrahydropyryl, tetrahydrothienyl, indolyl, quinolyl or isoquinolyl, it also being possible for the latter to be substituted by one or two identical or different radicals from the group comprising (C$_1$–C$_4$)-alkyl, (C$_1$–C$_4$)-alkoxy, (C$_1$–C$_4$)-alkoxycarbonyl, (C$_1$–C$_4$)-alkoxycarbonylamino, hydroxyl, amino, mono-or di-(C$_1$–C$_4$)-alkylamino and oxide;

R$^2$ and R$^{2*}$ are each, independently of one another,
hydrogen,
carboxyl,
(C$_1$–C$_8$)-alkyl which is optionally substituted by up to 2 identical or different radicals from the series comprising
hydroxyl,
(C$_1$–C$_4$)-alkoxy,
(C$_1$–C$_4$)-alkylthio,
(C$_1$–C$_4$)-alkylsulfinyl,
(C$_1$–C$_4$)-alkylsulfonyl,
(C$_1$–C$_4$)-alkanoyloxy,
carboxyl,
(C$_1$–C$_4$)-alkoxycarbonyl,
amino,
amidino,
guanidino,
N,N'-di-(benzyloxycarbonyl)-guanidino,
carbamoyl,
(C$_6$–C$_{10}$)-aryl-(C$_1$–C$_3$)-alkoxycarbonyl,
(C$_1$–C$_5$)-alkoxycarbonylamino,
(C$_6$–C$_{10}$)-aryl-(C$_1$–C$_3$)-alkoxycarbonylamino or
(C$_3$–C$_{10}$)-cycloalkyl,
(C$_3$–C$_{10}$)-cycloalkyl-(C$_1$–C$_3$)-alkyl,
(C$_6$–C$_{10}$)-aryl,
(C$_6$–C$_{10}$)-aryl-(C$_1$–C$_3$)-alkyl, where the aryl moiety is in each case optionally substituted by one, two or three identical or different radicals from the series comprising
F, Cl, Br,
hydroxyl,
(C$_1$–C$_4$)-alkoxy,
(C$_1$–C$_4$)-alkyl,
(C$_1$–C$_4$)-alkoxycarbonyl and
amino or
Het-(C$_1$–C$_4$)-alkyl, where Het is defined as for R$^1$ and R$^{1*}$, or is furyl, pyrazolyl, benzothienyl, indolyl or thienyl;

and R$^3$ are R$^{3*}$ each, independently of one another,
hydrogen or
methyl;

R$^4$ and R$^{4*}$ are each, independently of one another,
hydrogen or
methyl;

R$^5$, R$^6$ and R$^7$ are defined as described on pages 18/19;

$R^8$ and $R^{8*}$ are each, independently of one another,
hydrogen,
methyl, ethyl or n-propyl or form, together with $R^9$ and $R^{9*}$, respectively, and the atoms carrying them, a 1,2,3,4-tetrahydroisoquinoline or a 2-azabicyclooctane framework;

$R^9$ and $R^{9*}$ are each, independently of one another, defined as for $R^2$ and $R^{2*}$, or are $(C_1-C_8)$-alkanoyloxy, or form, together with $R^{10}$ and $R^{10*}$, respectively, and the atoms carrying them, cyclic ring systems with 5 to 7 ring members; or form, together with $R^{11}$ and $R^{11*}$, respectively, a thiochroman system whose sulfur atom can optionally be oxidized to the sulfone;

$R^{10}$ and $R^{10*}$ are each, independently of one another, hydrogen or methyl;

$R^{11}$ and $R^{11*}$ are as defined on page 19; where one or more amide groups (—CONH—) in the main chain in the abovementioned compounds of the formula I can be replaced as defined on page 20;

$R^{14}$ is
hydrogen or
methyl;
and the physiologically tolerated salts thereof.

Further particularly preferred compounds of the formula I are those in which

Q is a radical of the formula IIa;

$R^1$ and $R^{1*}$ are each, independently of one another,
hydrogen,
carboxyl,
$(C_1-C_8)$-alkylsulfonyl such as
methylsulfonyl,
tert.-butylsulfonyl or
isopropylsufonyl,
$(C_1-C_8)$-alkylsulfinyl,
$(C_1-C_8)$-mono-, di- or trihydroxyalkylsulfonyl such as
2-hydroxyethylsulfonyl or
2-hydroxypropylsulfonyl,
hydroxy-$(C_1-C_{10})$-alkanoyl, such as
2-hydroxypropionyl,
3-hydroxypropionyl,
3-hydroxybutyryl or
2-hydroxy-3-methylbutyryl,
mono-, di-, tri- or tetra-hydroxy-$(C_1-C_4)$-alkyl, such as
1,2,3-trihydroxypropyl,
1,2-dihydroxyethyl or
hydroxymethyl,
$(C_1-C_8)$-alkanoyloxy-$(C_1-C_{10})$-alkyl such as
acetoxymethyl,
1,2-diacetoxyethyl,
1,2,3-triacetoxypropyl,
$(C_1-C_{11})$-alkanoyl, such as
n-decanoyl,
formyl,
acetyl,
propionyl,
pivaloyl,
isovaleryl or
isobutyryl,
amino-$(C_1-C_{11})$-alkanoyl, such as
3-amino-3,3-dimethylpropionyl,
4-aminobutyryl,
5-aminopentanoyl,
6-aminohexanoyl, N-$(C_1-C_4)$-alkoxycarbonylamino-$(C_1-C_8)$-alkyl, such as
4-N-tert.-butoxycarbonylaminobutyryl,
5-N-tert.-butoxycarbonylaminopentanoyl,
6-N-tert.-butoxycarbonylaminohexanoyl,
di-$(C_1-C_7)$-alkylamino-$(C_2-C_{11})$-alkanoyl, such as
dimethylaminoacetyl,
$(C_3-C_9)$-cycloalkylcarbonyl, such as
cyclopropylcarbonyl,
cyclobutylcarbonyl,
cyclopentylcarbonyl or
cyclohexylcarbonyl,
amino-$(C_3-C_8)$-cycloalkylcarbonyl, such as
2-aminocyclopropylcarbonyl,
3-aminocyclobutylcarbonyl,
3-aminocyclopentylcarbonyl,
4-aminocyclohexylcarbonyl,
amino-$(C_3-C_8)$-cycloalkylsulfonyl, such as
3-aminocyclopentylsulfonyl,
4-aminocyclohexylsulfonyl,
phenyl,
triphenyl-$(C_1-C_2)$-alkyl, such as
triphenylmethyl,
2-triphenylethyl
$(C_6-C_{10})$-aryl-$(C_1-C_4)$-alkyl such as
benzyl,
2-phenylethyl or
1-naphthylmethyl,
$(C_6-C_{10})$-aryl-$(C_2-C_{11})$-alkanoyl, such as
phenylacetyl,
phenylpropanoyl or
phenylbutanoyl,
benzoyl or benzenesulfonyl, each of which is optionally substituted by halogen, amino, $(C_1-C_7)$-alkyl, $(C_1-C_7)$-alkoxy or $(C_1-C_7)$-alkoxycarbonyl, such as
4-chlorobenzoyl,
4-methylbenzoyl,
2-methoxycarbonylbenzoyl,
4-methoxybenzoyl,
benzenesulfonyl,
4-methylphenylsulfonyl,
benzylsulfonyl, benzylsulfinyl or benzylthio, each of which is optionally substituted by halogen, amino, $(C_1-C_7)$-alkyl, $(C_1-C_7)$-alkoxy or $(C_1-C_7)$-alkoxycarbonyl, such as
4-chlorobenzylsulfonyl,
benzylsulfinyl,
4-chlorobenzylthio,
amino,
$(C_1-C_4)$-alkoxycarbonylamino,
$(C_1-C_{12})$-alkanoyl which is substituted by hydroxyl, amino and optionally by phenyl or cyclohexyl, such as
2-amino-1-hydroxy-4-methylpentyl,
optionally protected amino-substituted $(C_6-C_{10})$-aryl- or $(C_3-C_{10})$-cycloalkyl-$(C_1-C_4)$-alkyl or $(C_1-C_8)$-alkyl, such as
2-amino-3-phenylpropyl or
N-tert.-butoxycarbonyl-2-amino-3-phenylpropyl,
$(C_1-C_{10})$-alkoxycarbonyl such as
methoxycarbonyl,
ethoxycarbonyl,
isobutoxycarbonyl or
tert.-butoxycarbonyl,
substituted $(C_1-C_{10})$-alkoxycarbonyl, such as
2-(trimethylsilyl)ethoxycarbonyl,
2,2,2-trichloroethoxycarbonyl, 1,1-dimethyl-2,2,2-trichioroethoxycarbonyl,
($C_6$–$C_{14}$)-aryl-($C_1$–$C_6$)-alkoxycarbonyl, such as
benzyloxycarbonyl,
1- or 2-naphthylmethoxycarbonyl or
9-fluorenylmethoxycarbonyl,
1-deoxyhexoketosyl or 1-deoxypentoketosyl such as
1-deoxyfructos-1-yl, 1-deoxysorbos-1-yl or
1-deoxyribulos- 1-yl
hexosyl or pentosyl, such as
mannosyl, glucosyl or galactosyl,
xylosyl, ribosyl or arabinosyl,
6-deoxyhexosyl, such as
rhamnosyl, fucosyl or deoxyglucosyl,
amino sugar residues, such as
2-amino-2-deoxyglucosyl,
2-acetamido-2-deoxyglucos yl,
2-amino-2-deoxygalactosyl or
2-acetamido-2-deoxygalactosyl,
lactosyl,
maltosyl, it being possible for the linked sugars to be in
the pyranose or the furanose form,
Het-carbonyl or Het-sulfonyl, such as
piperidino-4-carbonyl,
morpholino-4-carbonyl,
pyrrolyl-2-carbonyl,
pyridyl-3-carbonyl,
4-tert.-butoxycarbonylamino-1-piperidylcarbonyl,
4-amino-1-piperidylcarbonyl,
4-tert.-butoxycarbonylamino-1-piperidylsulfonyl,
4-amino-1-piperidylsulfonyl,
Het-($C_1$–$C_6$)-alkyl, such as
2-pyridyl-($C_1$–$C_6$)-alkyl,
3-pyridyl-($C_1$–$C_4$)-alkyl,
4-pyridyl-($C_1$–$C_6$)-alkyl,
Het-($C_1$–$C_6$)-alkanoyl, such as
2-pyridyl-($C_1$–$C_6$)-alkanoyl,
3-pyridyl-($C_1$–$C_6$)-alkanoyl,
4-pyridyl-($C_1$–$C_6$)-alkanoyl,
Het-mercapto-($C_1$–$C_3$) -alkylcarbonyl, such as
2-pyridylthioacetyl, where Het is in each case
pyrrolyl,
imidazolyl,
pyridyl,
pyrimidyl,
pyrrolidyl,
piperidyl or
morpholino,
it also being possible for the latter to be substituted
by one or two identical or different radicals from
the group comprising ($C_1$–$C_4$)-alkyl, ($C_1$–$C_4$)-
alkoxycarbonyl, ($C_1$–$C_4$)-aikoxycarbonylamino,
hydroxyl, amino, mono-or di-($C_1$–$C_4$)-
alkylamino;
$R^2$ and $R^{2*}$ are each, independently of one another,
hydrogen,
carboxyl,
methyl, ethyl, isopropyl, n-propyl, n-butyl, isobutyl,
sec.-butyl, pentyl, hexyl,
cyclohexyl,
cyclopentylmethyl, cyclohexylmethyl,
cycloheptylmethyl,
4-methylcyclohexylmethyl,
1-decahydronaphthylmethyl,
2-decahydronaphthylmethyl,
phenyl,
benzyl,
2-phenylethyl,
1-naphthylmethyl, 2-naphthylmethyl,
2-methylbenzyl, 3-methylbenzyl, 4-methylbenzyl,
2,4,6-trimethylbenzyl,
4-tert.-butylbenzyl,
4-tert.-butoxybenzyl,
4-hydroxybenzyl,
4-methoxybenzyl,
2,4-dimethoxybenzyl,
3,4-dihydroxybenzyl,
3,4-dimethoxybenzyl,
(benzodioxolan-4-yl) methyl,
4-chlorobenzyl,
-hydroxymethyl,
1-hydroxyethyl,
2-pyridylmethyl, 3-pyridylmethyl, 4-pyridylmethyl,
2-(4-pyridyl)ethyl,
2-thienylmethyl, 3-thienylmethyl,
2-(2-thienyl)ethyl, 2-(3-thienyl)ethyl,
indol-2-ylmethyl, indol-3-ylmethyl,
(1-methylimidazol-4-yl) methyl,
imidazol-4-ylmethyl, imidazol-1-ylmethyl,
2-thiazolylmethyl,
3-pyrazolylmethyl,
4-pyrimidylmethyl,
2-benzo[b]thienylmethyl, 3-benzo[b]thienylmethyl,
2-furylmethyl,
2-(methylthio) ethyl,
2-(methylsulfinyl) ethyl,
2-(methylsulfonyl)ethyl,
$R^3$, $R^{3*}$, $R^4$, $R^{4*}$, $R^{10}$ and $R^{10*}$ are each hydrogen;
$R^5$ is
hydrogen,
($C_1$–$C_6$)-alkyl or
an equivalent of a pharmaceutically tolerated cation;
$R^6$ is oxygen;
$R^8$ and $R^{8*}$ are each, independently of one another,
hydrogen or form, together with $R^9$ and $R^{9*}$,
respectively, and the atoms carrying them, a 1,2,3,
4-tetrahydroisoquinoline or 2-azabicyclooctane
framework;
$R^9$ and $R^{9*}$ are each, independently of one another,
defined as $R^2$ and $R^{2*}$, respectively, or are
hydroxyl,
acetoxy,
tert.-butoxymethyl,
3-guanidinopropyl,
carbamoylmethyl, carbamoylethyl,
carboxymethyl, carboxyethyl,
mercaptomethyl,
(1-mercapto-1-methyl)ethyl,
aminomethyl, 2-aminoethyl, 3-aminopropyl,
4-aminobutyl,
N,N-dimethylamino,
N,N'-di-(benzyloxycarbonyl)guanidinopropyl,
2-benzyloxycarbonylethyl, benzyloxycarbonylmethyl
or
4-benzylcarbonylaminobutyl;
$R^{11}$ and $R^{11*}$ are each, independently of one another,
hydrogen,
hydroxyl or
acetoxy;
it being possible for one or more amide groups
(—CONH—) in the main chain in the abovementioned
compounds of this invention to be replaced by
—$CH_2NR_{14}$— or —$CH(OH)CH_2$—;
$R^{14}$ is hydrogen or methyl;

and the physiologically tolerated salts thereof.

Very particularly preferred compounds of the formula I are those in which

Q is a radical of the formula IIa;

$R^1$ and $R^{1*}$ are each, independently of one another,
hydrogen,
carboxyl,
($C_1$–$C_8$)-alkylsulfonyl, such as
  methylsulfonyl,
  tert.-butylsulfonyl or
  isopropylsulfonyl,
($C_1$–$C_8$)-mono- or dihydroxyalkylsulfonyl, such as
  2-hydroxyethylsulfonyl or
  2-hydroxypropylsulfonyl,
mono-, di- or trihydroxy-($C_1$–$C_3$)-alkyl, such as
  1,2,3-trihydroxypropyl,
  1,2-dihydroxyethyl or
  hydroxymethyl,
($C_1$–$C_8$)-alkoxycarbonyl, such as
  methoxycarbonyl,
  ethoxycarbonyl,
  isobutoxycarbonyl or
  tert.-butoxycarbonyl,
($C_6$–$C_{10}$)-aryl-($C_1$–$C_4$)-alkoxycarbonyl, such as
  benzyloxycarbonyl or
  1- or 2-naphthylmethoxycarbonyl,
9-fluorenylmethoxycarbonyl,
($C_1$–$C_4$)-alkanoyloxy-($C_1$–$C_6$)-alkyl, such as
  acetoxymethyl,
  1,2-diacetoxyethyl,
  1,2,3-triacetoxypropyl,
  phenyl,
  triphenylmethyl,
($C_6$–$C_{10}$)-aryl-($C_1$–$C_4$)-alkyl such as
  benzyl,
benzenesulfonyl which is optionally substituted by
  halogen, amino, ($C_1$–$C_4$)-alkyl or methoxy, such as
  benzenesulfonyl,
  4-methylphenylsulfonyl,
benzylsulfonyl, -sulfinyl or -thio which is optionally substituted by halogen, amino, ($C_1$–$C_4$)-alkyl or methoxy, such as
  4-chlorobenzylsulfonyl,
  benzylsulfinyl or
  4-chlorobenzylthio,
Het-carbonyl or Het-sulfonyl, such as
  4-tert.-butoxycarbonylamino- 1-piperidylcarbonyl,
  4-amino- 1-piperidylcarbonyl,
  4-tert.-butoxycarbonylamino- 1-piperidylsulfonyl,
  4-amino-1-piperidylsulfonyl,
Het-($C_1$–$C_4$)-alkanoyl, such as
  2-pyridylacetyl or
  3-pyridylacetyl,
Het-mercapto-($C_1$–$C_3$)-alkylcarbonyl, such as
  2-pyridylthioacetyl, where Her is in each case
  pyrrolyl,
  imidazolyl,
  pyridyl,
  pyrimidyl,
  pyrrolidyl,
  piperidyl or
  morpholino,
  it also being possible for this radical to be substituted by one or two identical or different radicals from the group comprising methyl, amino and ($C_1$–$C_4$) -alkoxycarbonylamino,
amino-($C_3$–$C_6$)-cycloalkylcarbonyl, such as
  2-aminocyclopropylcarbonyl,
  3-aminocyclobutylcarbonyl,
  3-aminocyclopentylcarbonyl,
  4-aminocyclohexylcarbonyl,
($C_1$–$C_8$)-alkanoyl, which is substituted by hydroxyl and amino and optionally by phenyl or cyclohexyl, such as
  2-amino- 1-hydroxy-4-methylpentyl,
optionally protected amino-substituted phenyl- or cyclohexyl-($C_1$–$C_6$)-alkyl, such as
  2-amino-3-phenylpropyl or
  N -tert.-butoxycarbonyl-2-amino-3-phenylpropyl,
amino,
($C_1$–$C_4$)-alkoxycarbonylamino,
benzyloxycarbonylamino,
1-deoxyhexoketosyl or 1-deoxypentoketosyl, such as
  1-deoxyfructos-1-yl, 1-deoxysorbos-1-yl or
  1-deoxyribulos-1-yl,
hexosyl or pentosyl, such as
  mannosyl, glucosyl or galactosyl, or
  xylosyl, ribosyl or arabinosyl, it being possible for the linked sugars to be in the pyranose or the furanose form, $R^2$ and $R^{2*}$ are each, independently of one another,
  hydrogen, methyl, ethyl, isopropyl, n-propyl, n-butyl, isobutyl, sec.-butyl, pentyl, hexyl,
  cyclopentylmethyl, cyclohexylmethyl,
  4-methylcyclohexylmethyl,
  phenyl,
  benzyl,
  2-phenylethyl,
  1-naphthylmethyl, 2-naphthylmethyl,
  2-methylbenzyl, 3-methylbenzyl, 4-methylbenzyl,
  2,4,6-trimethylbenzyl,
  4-tert.-butylbenzyl,
  4-methoxybenzyl,
  3,4-dihydroxybenzyl,
  3,4-dimethoxybenzyl,
  2-pyridylmethyl, 3-pyridylmethyl, 4-pyridylmethyl or
  2-(4-pyridyl) ethyl, $R^3$, $R^{3*}$, $R^4$, $R^{4*}$, $R^{10}$ and $R^{10*}$ are each hydrogen;

$R^5$ and $R^6$ are defined as described on pages 28/29;

$R^8$ and $R^{8*}$ are each, independently of one another,
  hydrogen or form, together with $R^9$ and $R^{9*}$, respectively, and the atoms carrying them, a 1,2,3, 4-tetrahydroisoquinoline or 2-azabicyclooctane framework;

$R^9$ and $R^{9*}$ are each, independently of one another, defined as $R^9$ and $R^{9*}$, respectively, on page 29;

$R^{11}$ and $R^{11*}$ are each, independently of one another,
  hydrogen
  hydroxyl or
  acetoxy;

it being possible for one or more amide groups (—CONH—) in the main chain in the abovementioned compounds of the invention to be replaced by —CH$_2$NH— or —CH(OH)CH$_2$—;

and the physiologically tolerated salts thereof.

Further especially preferred compounds of the formula I are those in which the radicals and symbols with and without the asterisk are identical in each case, Q is a radical of the formula IIa, Y is oxygen, A is a radical of the formula IV, where E, F or G is Gly, Ala, Val, Leu, Ile, Nva, Nle, Phe, Tyr, Asp or Glu and n+o+p is 0 or 1, D is $R^1$ or a radical of the formulae V or VI, $R^1$ is hydrogen, $(C_1-C_6)$-alkylsulfonyl, $(C_6-C_{10})$-aryl-$(C_1-C_2)$-alkyl, triphenylmethyl, $(C_1-C_6)$-alkoxycarbonyl or $(C_6-C_{10})$-aryl-$(C_1-C_2)$-alkoxycarbonyl, $R^9$ is hydrogen, phenyl or benzyl, $R^3$, $R_4$, $R^8$, $R^{10}$ and $R^{11}$ are hydrogen, $R^6$ is oxygen and $R^9$ is hydrogen, n-propyl, isopropyl, n-butyl, sec.-butyl, isobutyl, benzyl, carboxymethyl, carboxyethyl, 1-naphthylmethyl, 2-naphthylmethyl, 2-(methylthio)ethyl, 2-(methylsufonyl)ethyl, 2- (methylsulfonyl)ethyl, indol-2-yl-methyl or indol-3-yl-methyl and the physiologically tolerated salts thereof.

Compounds which may likewise be mentioned as very preferred are those of the formula I in which the radicals and symbols with and without the asterisk are identical in each case, Q is a radical of the formula IIa, Y is oxygen, A is a radical of the formula IV, where E, F or G is Val, Phe, Ile or Asp and n+o+p is 0 or 1, D is $R^1$ or a radical of the formulae V or VI, $R^1$ is hydrogen, $(C_1-C_6)$-alkylsulfonyl, phenyl-$(C_1-C_2)$-alkyl, triphenylmethyl, $(C_1-C_6)$-alkoxycarbonyl or phenyl-$(C_1-C_2)$-alkoxycarbonyl, $R^2$ is hydrogen, phenyl or benzyl, $R^3$, $R^4$, $R^8$, $R^{10}$ and $R^{11}$ are hydrogen, $R^5$ is hydrogen or $(C_1-C_4)$-alkyl, $R^6$ is oxygen and $R^9$ is hydrogen, isopropyl, sec.-butyl, benzyl, carboxymethyl, 1-naphthylmethyl, 2-(methylthio)ethyl or indol-2-yl-methyl and the physiologically tolerated salts thereof.

The present invention also relates to a process for the preparation of compounds of the formula (I), which comprises coupling a fragment with a terminal carboxyl group, or the reactive derivative thereof, to a corresponding fragment with a free amino group, where appropriate eliminating (a) protective group(s) temporarily introduced to protect other functional groups, and converting the compound obtained in this way where appropriate into its physiologically tolerated salt.

Fragments of a compound of the formula (I) with a terminal carboxyl group have, for example, the following formulae:

| | |
|---|---|
| D—OH | (VIII) |
| D—E—OH | (IX) |
| D—F—OH | (X) |
| D—G—OH | (XI) |
| D—E—F—OH | (XII) |
| D—E—G—OH | (XIII) |
| D—F—G—OH | (XIV) |
| D—E—F—G—OH | (XIVa) |

A corresponding statement applies to the analogous radicals with an asterisk.

Fragments of a compound of the formula (I) with a terminal amino group have, for example, the following formulae:

| | |
|---|---|
| H—Z—H | (XV) |
| H—G—Z—G*—H | (XVI) |
| H—F—Z—F*—H | (XVIa) |
| H—E—Z—E*—H | (XVIb) |
| H—F—G—Z—G*—F*—H | (XVII) |
| H—E—G—Z—G*—E*—H | (XVIIa) |
| H—E—F—Z—F*—E*—H | (XVIIb) |
| H—E—F—G—Z—G*—F*—E*—H | (XVIII) | where Z is a radical of the formula (XIX):

(XIX)

Where the target molecules are not symmetric, it is also possible to use other fragments apart from those of the formulae XV to XVIII, which are possibly protected on a terminal amino group.

Methods suitable for producing an amide linkage are described, for example, in Houben-Weyl, Methoden der organischen Chemie, volume 15/2; Bodanszky et al., Peptide Synthesis. 2nd ed. (Wiley & Sons, New York 1976) or Gross, Meienhofer, The Peptides: Analysis, synthesis, biology (Academic Press, New York 1979). The following methods are preferably employed: active ester method with N-hydroxysuccinimide, 1-hydroxybenzotriazole or 3-hydroxy-4-oxo-3,4-dihydro-1,2,3-benzotriazine as alcohol component, coupling with a carbodiimide such as dicyclohexylcarbodiimide (DCC) or with n-propanephosphonic anhydride (PPA) and the mixed anhydride method with pivaloyl chloride or ethyl or isobutyl chloroformate, or coupling with phosphonium reagents such as benzotriazol-1-yloxytris(dimethylamino)phosphonium hexafluorophosphate (BOP) or uranium reagents such as 2-(1H-benzotriazole-1-yl)-1,1,3,3-tetramethyluronium tetrafluoroborate (TBTU).

Fragments of the formula (VIII) or (VIII*) which are a) covered by formula (V) or (V*) are synthesized by the general methods for preparing amino acids;

b) covered by formula (VI) or (VI*) are synthesized, for example, starting from the corresponding amino acids, with retention of the center of chirality thereof. Diazotization at −20° C. to 50° C. in dilute mineral acids leads to e-bromo carboxylic acids or, via the lactic acids, to e-trifluoromethanesulfonyloxy carboxylic acids which can be reacted with a nucleophile carrying $R^1$ and $R^{11}$ or $R^{1*}$ and $R^{11*}$, or are prepared, for example, starting from malonic esters whose alkylation provides mono- or disubstituted malonic esters which are converted into the desired derivatives after hydrolysis by decarboxylation.

c) covered by formula (VII) or (VII*) are synthesized starting from the corresponding α-amino acids, with retention of the center of chirality thereof. Diazotization at −20° C. to 50° C. in dilute mineral acids leads to lactic acids which can be reacted with an electrophile carrying $R^1$ or $R^{1*}$.

Fragments of the formulae (IX), (X), (XI), (XII) and (XIII), (XIV) and (XIVa) are synthesized by the general, known methods for the preparation of amino acids and peptides.

Fragments of the formula XV are synthesized by known processes (K. Sasse in Houben-Weyl, Methoden der organischen Chemie, volume 12/1, Georg Thieme Verlag, Stuttgart, 1963; U.-H. Felcht in Houben-Weyl, Methoden der organischen Ctqemie, volume 12/E/2, George Thieme Verlag, Stuttgart, 1982; D. Redmore in Griffiths, ed., Phosphorus Chemistry, vol. 8, page 515). The following methods are preferably employed:

1) Synthesis of the compounds of the formula XVa

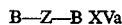

where B is benzyl, by known methods, for example by reaction of hypophosphorous acid or hypophosphorous esters (S. J. Fitch, J. Am. Chem. Soc. 86 (1964) 61) with Schiff's bases (H. Schmidt, Ber. 81 (1948) 477; W. M. Linfield et al. J. Org. Chem. 26 (1961) 4088) from aldehydes and benzylamine Mannich bases (L. Maier, Helv. Chim. Acta 50 (1967) 1742) from aldehydes and dibenzylamine aldehydes to give the corresponding 1-substituted bis(hydroxymethyl) phosphonous acids (V. Ettel et al., Collect. Czech. Chem. Commun. 26 (1961) 2087) and replacement of the hydroxyl groups by the benzylamino group by known processes (K. Sasse in Houben-Weyl, Methoden der organischen Chemie, volume 12/1, Georg Thieme Verlag, Stuttgart, 1963; U.-H. Felcht in Houben-Weyl, Methoden der organischen Chemie, volume 12/E/2, George Thieme Verlag, Stuttgart, 1982; D. Redmore in Griffiths, ed., Phosphorus Chemistry, vol. 8, page 515).

Synthesis of the compounds of the formula XV by catalytic hydrogenation of the compounds of the formula XVa by known methods (T. W. Greene, Protective Groups in Organic Synthesis, J. Wiley & Sons, New York 1981).

The fragments of the formulae XVI, XVII and XVIII are synthesized by generally known methods for the preparation of amino acids and peptides.

One or more amide groups in the compounds of the formula I can be replaced by $-CH_2NR^{14}-$, $-CH_2S-$, $-CH_2O-$, $OCH_2-$, $-CH_2CH_2-$, $-CH=CH-$ (cis and trans), $-COCH_2-$, $-CH(OH)CH_2-$, $-CH_2SO-$, $-CH_2SO_2-$, $-COO-$, $-P(O)(OR^{15})CH_2-$, $-P(O)(OR^{15})_2NH-$ or $-NH-CO-$.

Compounds of the formula XVb

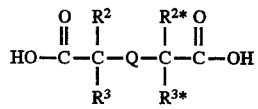

can be obtained by known processes (K. Sasse in Houben-Weyl, Methoden der organischen Chemie, volume 12/1, Georg Thieme Verlag, Stuttgart, 1963; U.-H. Felcht in Houben-Weyl, Methoden der organischen Chemie, volume 12/E/2, George Thieme Verlag, Stuttgart, 1982), preferably by radical addition of hypophosphorous acid or hypophosphorous salts onto olefins.

Peptide analogs of this type can be prepared by known processes which can be found, for example, in the following places in the literature:

A.F. Spatola in Chemistry and Biochemistry of Amino Acids Peptides and Proteins 1983 (B. Weinstein et al. eds.)

Marcel Dekker, New York, p. 267 (review article);

J.S. Morley, Trends Pharm Sci. (1980) p. 463–468 (review article);

D. Hudson et al., Int. J. Pept. Prot. Res. (1979), 14, 177–185 ($-CH_2NH-$, $-CH_2CH_2-$);

A.F. Spatola et al., Ufe Sci. (1986), 38, 1243–1249 ($-CH_2-S-$);

M. M. Hann, J. Chem. Soc. Perkin Trans. I (1982) 307–314 ($-CH=CH-$, cis and trans);

J. K. Whitesell et al., Chirality 1, (1989) 89–91 ($-CH=CH-$trans)

R. G. Almquist et al., J. Med. Chem. (1980), 23, 1392–1398 ($-COCH_2-$);

C. Jennings-White et al., Tetrahedron Lett. (1982) 23, 2533 ($-COCH_2-$);

M. Szelke et al., EP-A 45665 (1982), CA: 97:39405 ($-CH(OH)CH_2-$);

M. W. Holladay et al., Tetrahedron Lett. (1983) 24, 4401–4404 ($-CH(OH)CH_2-$);

V. J. Hruby, Life Sci. (1982), 31,189–199 ($-CH_2-S-$);

N. E. Jacobsen, P. A. Barlett, J. Am. Chem. Soc. (1981) 103, 654–657 ($-P(O)(OR)NH-$).

The necessary operations preceding and following the preparation of the compounds of the formula I, such as the introduction and elimination of protective groups, are known from the literature and described, for example, in T. W. "Greene Protective Groups in Organic Synthesis" (John Wiley & Sons, New York, 1981). Salts of compounds of the formula I with salt-forming groups are prepared in a manner known per se, for example by reacting a compound of the formula I with a basic group with a stoichiometric amount of a suitable acid or compounds of the formula I with an acidic group with a stoichiometric amount of a suitable base. Mixtures of stereoisomers, especially mixtures of diastereomers, which may be produced in the synthesis of compounds of the formula I, can be separated in a manner known per se by fractional crystallization or by chromatography.

The compounds of the formula (I) according to the invention have enzyme-inhibitory properties. In particular, they inhibit the action of retroviral aspartyl proteases such as that of HIV protease. Their enzyme-inhibitory action, which is in the milli- to subnanomolar range, can be determined as follows.

Principle of the assay:

A substrate of HIV protease which has been used to date is, inter alia, the heptapeptide: H-Ser-Phe-Asn-Phe-Pro-Gln-Ile-OH (P.L. Darke et al., Biophys. Res. Commun. 156 (1988) 297–303). HIV protease cleaves the substrate between the second Phe and Pro.

It has now been found, surprisingly, that replacement of proline by 5-oxaproline in this sequence leads to a substrate which can be cleaved considerably more rapidly by HIV protease and thus permits more rapid analysis with less enzyme being required.

General procedure for testing inhibitors of HIV proteases:
a) Preparation of the substrate solution:
  2 mg of H-Ser-Phe-Asn-Phe-Opr-Gln-Ile-OH (H-Opr-OH=5-oxaproline) are dissolved in 1 ml of MGTE15 buffer (possibly using ultrasound) and subsequently filtered through a sterile filter (0.45 μm).

b) Preparation of the inhibitor solution:

2.5 times the desired molarity of the inhibitor are weighed into each ml of solution and dissolved in DMSO (10% of the final volume). The solution is diluted with MGTE15 buffer to the final volume and filtered through a sterile filter (0.45 μm).

c) Preparation of the protease solution:

5 μl of HIV protease solution are diluted as required with MGTE25 buffer.

d) Assay procedure:

10 μl samples of the substrate solution are pipetted into test tubes (16×100) with screw caps. For the blanks, 10 μl of MGTE15 buffer containing 10% DMSO are pipetted in. 10 μl samples of the inhibitor solution are placed in the other test tubes. Each sample is incubated at 37° C. for 5–10 minutes and then 5 μl of the protease solution are added. After reaction at 37° C. for 2 hours, 10 or 20 μl (depending on the sensitivity of the HPLC apparatus) are removed from each sample by pipette, transferred into microvials and diluted with 120 μl of the HPLC solvent.

e) HPLC analysis conditions:

Solvent system: 80% 0.1M phosphoric acid pH 2.5
20% (w/w) acetonitrile
Column: Merck •LICHROSORB RP18 (5 μm) 250×4
Flow rate: 1 ml/min
Column temperature: 42° C.
Detector parameters: 215 nm, 0.08 AUF, 18.2 ° C.
Analysis time: 11 minutes
Retention time for the substrate: 8.1 minutes
Retention time for the N-terminal tetrapeptide: 3.9 minutes f) Solvents required:

1) MGTE 15 buffer:
  20 mM morpholinoethanesulfonic acid (MES)
  15% (w/v) glycerol
  0.1% (v/v) Triton×100
  5 mM EDTA
  0.5M NaCl
  1 mM phenylmethylsulfonyl fluoride (PMSF)

2) MGTE25 buffer:
  Composition similar to that for MGTE15 buffer with the following difference:
  25% (w/v) glycerol,
  plus 1 mM dithiothreitol (DTT). MES, EDTA, NaCl, DTT and PMSF are weighed into an Edenmeyer flask and dissolved in a little water, and the pH is adjusted to 6. The appropriate amount of glycerol is weighed into a graduated flask and •Triton×100 is pipetted in. The aqueous solution is transferred into the graduated flask, which is made up to the mark with water.

3) HPLC solvent:
  A 0.1M solution of ortho-phosphoric acid (FLUKA extra pure grade) is prepared. This solution is adjusted to exactly pH 2.5 with triethylamine (FLUKA extra pure grade). The weight of the solution is determined and the appropriate amount of acetonitrile (n.b. hood) is weighed in. Thoroughly mix and degas with 99.999% helium for about 5 minutes.

g) Evaluation:

Under the conditions chosen in this case, the heptapeptides are separated from the N-terminal tetrapeptide produced in the enzymatic cleavage. The % content of the tetrapeptide peak related to the total of tetrapeptide+heptapeptide corresponds to the proportion cleaved.

The target peptide was synthesized stepwise using the Fmoc method on a p-benzyloxybenzyl alcohol resin esterified with Fmoc-Ile-OH from Novabiochem (loading about 0.5 mmol/g of resin) and a model 430 A peptide synthesizer from Applied Biosystems. 1 g of the resin was employed, and the synthesis was carried out using a synthesis program modified for the Fmoc method.

The following amino-acid derivatives were used: Fmoc-Gln-OH, Fmoc-Opr-OH, Fmoc-Phe-OObt, Fmoc-Asn-OH and Fmoc-Ser(tBu)-OObt. To synthesize Fmoc-Opr-OH, the method of Vasella et al. (J. C. S. Chem. Comm. 1981, 97–98) was used to synthesize H-Opr-OtBu, which was reacted with Fmoc-OSu in dioxane/water (1:1) in the presence of $NaHCO3$. The subsequent cleavage of the tert.-butyl ester with trifluoroacetic acid provides Fmoc-Opr-OH.

In each case 1 mmol of the amino acid derivatives with free carboxyl group was weighed together with 0.95 mmol of HOObt into the cartridges of the synthesizer. These amino acids were preactivated directly in the cartridges by dissolving in 4 ml of DMF and adding 2 ml of a 0.55 molar solution of diisopropylcarbodiimide in DMF. The HOObt esters of the other amino acids were dissolved in 6 ml of NMP and then coupled just like the in situ preactivated amino acids to the resin which had previously been ableblocked with 20% piperidine in DMF. After the synthesis was complete, the peptide was cleaved off the resin, simultaneously removing the side-chain protective groups, with trifluoroacetic acid, using thioanisole and ethanedithiol as cation traps. The residue obtained after the trifluoroacetic acid had been stripped off was digested with ethyl acetate and centrifuged several times.

The remaining residue was chromatographed on an alkylated dextran gel with 10% strength acetic acid. The fractions containing the pure peptide were combined and freeze-dried.

Mass spectrum (FAB): 854 ($M+H^+$)

Amino-acid analysis Asp: 0.98; Ser: 0.80; Glu: 1.00; Ile: 1.05; Phe: 2.10; $NH_3$: 1.76.

The invention also relates to the use of the compounds of the formula I as medicines and pharmaceutical products which contain this compound. Use in primates, especially in humans, is preferred.

Pharmaceutical products contain an effective amount of the active compound of the formula I together with an inorganic or organic pharmaceutically utilizable excipient. Intranasal, intravenous, subcutaneous or oral use is possible. The dosage of the active compound depends on the warm-blooded species, the body weight, age and on the mode of administration.

The pharmaceutical products of the present invention are prepared in dissolving, mixing, granulating or coating processes known per se.

For a form for oral use, the active compounds are mixed with the additives customary for this purpose, such as excipients, stabilizers or inert diluents, and converted by customary methods into suitable dosage forms such as tablets, coated tablets, hard gelatin capsules, aqueous, alcoholic or oily suspensions, or aqueous, alcoholic or oily solutions. Examples of inert vehicles which can be used are gum arabic, magnesia, magnesium carbonate, potassium phosphate, lactose, glucose, magnesium stearyl fumarate or starch, especially corn starch. This preparation can take place both as dry or wet granules. Examples of suitable oily excipients or solvents are vegetable or animal oils, such as sunflower oil and fish liver oil.

For subcutaneous or intravenous administration, the active compounds or the physiologically tolerated salts thereof are converted, if desired with the substances customary for this purpose, such as solubilizers, emulsifiers or other auxiliaries, into solutions, suspensions or emulsions. Examples of suitable solvents are: water, physiological saline solutions or alcohols, for example ethanol, propanediol or glycerol, as well as sugar solutions such as glucose or mannitol solutions, or else a mixture of the various solvents mentioned.

It is likewise possible to employ injectable depot formulations. Examples of drug forms which can be used are oily crystal suspensions, microcapsules, rods or implants, it being possible for the latter to be composed of tissue-compatible polymers, especially biodegradable polymers, such as, for example, based on polylactic acid-polyglycolic acid copolymers or human albumins.

List of abbreviations:

| Boc | tert.-butyloxycarbonyl |
|---|---|
| Chg | cyclohexylglycyl |
| d | doublet |
| TLC | thin-layer chromatography |
| DCC | dicyclohexylcarbodiimide |
| DCM | dichloromethane |
| DMF | dimethylformamide |
| DMAP | 4-dimethylaminopyridine |
| DMSO | dimethyl sulfoxide |
| EDAC | 1-(3-dimethylaminopropyl)-3-ethylcarbodiimide hydrochloride |
| EA | ethyl acetate |
| FAB | fast atom bombardment |
| HOBt | hydroxybenzotriazole |
| i. Vac | in vacuo |
| m | multiplet |
| M | molecular peak |
| NEM | N-ethylmorpholine |
| Npg | neopentylglycyl |
| MS | mass spectrum |
| PPA | n-propylphosphonic anhydride |
| RT | room temperature |
| s | singlet |
| m.p. | melting point |
| t | triplet |
| Tbg | tert.-butylglycyl |
| TBTU | 2-(1H-benzotriazol-1-yl)-1,1,3,3-tetramethyluronium tetrafluoroborate |
| THF | tetrahydrofuran |
| Thia | 2-thienylalanyl |
| Z | benzyloxycarbonyl |

The other abbreviations used for amino acids correspond to the three-letter code customary in peptide chemistry (as is described, for example, in Eur. J. Biochem. 138, (1984), 9–37). Unless expressly indicated otherwise, an amino acid is always in the L configuration.

The examples which follow serve to illustrate the present invention without intending to restrict it to them.

EXAMPLE 1a

Bis(tert.-butoxycarbonyl-L-valyl-aminomethyl) phosphinic acid

Bis(hydroxymethyl)phosphinic acid

A mixture of 100 g (0.76 mol) of $H_3PO_2$ (50%), 500 ml of concentrated HCl and 47.5 g (1.58 mol) of paraformaldehyde is stirred first at 60° C. for 2 h and then under reflux for three days. After cooling, the water is stripped off in a rotary evaporator, and the residue is coevaporated four more times with toluene. The residue is the product (86 g, 90%) in the form of a viscous oil which was reacted further without further purification.

Bis(chloromethyl)phosphinic chloride 80 g (0.63 mol) of bis(hydroxymethyl)phosphinic acid are added dropwise to 500 g of boiling $SOCl_2$ while stirring. After addition is complete, the mixture is boiled under reflux for a further 3 hours. Excess thionyl chloride is removed by distillation under atmospheric pressure, and the residue is fractionated by fractional distillation. The product boiled at 85°–98° C./3–3.5 mm (yield: 91 g, 79%).

Bis(chloromethyl)phosphinic acid 17 g (94 mmol) of the resulting acid chloride are added dropwise, while stirring, to 20 ml of distilled water and stirred at room temperature for 1 h. The mixture is then filtered, and the flitrate is evaporated to dryness. The residue is a white solid (m.p.: 75°–78° C.). (Yield: 12.5 g; 82%).

Bis(benzylaminomethyl)phosphinic acid hydrochloride 12 g (74 mmol) of bis(chloromethyl)phosphinic acid are added slowly to 80 g of benzylamine at room temperature while stirring, during which the temperature increases slightly. The mixture is then heated at 115° C. for 24 h. Excess benzylamine is removed by distillation in vacuo, and the white residue is dissolved in 150 ml of distilled water, filtered and mixed with 30 mi of concentrated HCl and stirred at room temperature for 1 h. The white precipitate is filtered off with suction, washed with water and dried over $P_2O_5$. Yield: 20 g (79%); m.p.: 254° C.

Bis(aminomethyl)phosphinic acid hydrochloride 20 g (59 mmol) of bis(benzylaminomethyl)phosphinic acid hydrochloride are dissolved in 500 ml of glacial acetic acid and hydrogenated with $H_2$ and with 3 g of Pd/C (5%) for three days. The catalyst is filtered off and extracted with water in a Soxhlet. The water is concentrated, when the product separates out (yield: 6.2 g (66%); m.p.: 290° C.).

Bis(tert.-butoxycarbonyl-L-valyl-aminomethyl)phosphinic acid 37 mg of bis(aminomethyl)phosphonous acid hydrochloride were dissolved together with 98 mg of N-tert.-butoxycarbonyl-L-valine, 0.57 ml of NEM and 60 mg of HOBt in 2 ml of DMF. Addition of 85 mg of EDAC at 0° C. was followed by stirring at this temperature for a further hour and then at RT overnight. The solvent was removed in a rotary evaporator in vacuo, and the residue was purified by chromatography on silica gel. The yield was 97 mg (81%).

MS (FAB): 523 (M+H)$^+$, 423, 323

EXAMPLE 1b

Alternative preparation of N,N'-bis(tert.-butoxycarbonyl-L-valyl-aminomethyl) phosphinic acid Bis(aminomethyl)phosphinic acid hydrochloride was synthesized as described above by the method of DE 28 05 074.

N,N'-Bis(tert.-butoxycarbonyl-valyl-aminomethyl) phosphinic acid 3.45 g (30 mmol) of NEM was slowly added dropwise at 0° C. to 6.52 g (30 mmol) of N-tert.- butoxycarbonyl-L-valine and 9.63 g (30 mmol) TBTU in 70 ml of DMF. After addition was complete, the mixture was stirred for a further 15 minutes at 0° C. Subsequently, likewise at 0° C., 1.6 g (10 mmol) of bis(aminomethyl)phosphinic acid hydrochloride dissolved in 70 ml of water were added dropwise. The cooling was removed and the mixture was stirred at room temperature for a further 5 hours. The solvent was removed in a rotary evaporator, and the residue was purified by chromatography on silica gel ($CH_2Cl_2/CH_3OH/AcOH$: 18/1/1).

Yield: 46%;
$^1$H-NMR (270 MHz/DMSO/TMS): 0.82 (dd, 12H); 1.37 (s, 18H), 1.95 (m, 2H); 3.03 (d, broad, 4H, $J_{PH}$=10 Hz); 3.81 (dd, 2H), 6.74 (d, broad, 2H); 7.75 (s, broad, 2H);
MS (FAB): 567 (M+2Na-H)$^+$, 545 (M+Na)$^+$

EXAMPLE 2

Bis(tert.-butoxycarbonyl-L-phenylalanyl-aminomethyl)-Phosphinic acid

Synthesis in analogy to Example 1 from bis(aminomethyl)phosphinic acid hydrochloride and tert.-butoxycarbonyl-L-phenylalanine
MS (FAB): 619 (M+H)$^+$, 519, 419

EXAMPLE 3

N,N'-Bis(L-phenylalanyl-aminomethyl)phosphinic acid hydrochloride 220 mg (0.35 mmol) of N,N'-bis(tert.-butoxycarbonyl-L-phenylalanyl-aminomethyl)phosphinic acid were stirred in 10 ml of a 3N solution of HCl in 1/1 dioxane/methanol at room temperature for 1 h. The volatile constituents in the solution were removed in vacuo, and the residue was employed in the next stage without further purification. Yield: 112 mg (82%).
MS (FAB): 391 (M+H)$^+$ Example 4

N,N'-Bis[2S—((1,1-dimethylethylsulfonylmethyl)-3-(1-naphthyl)propionyl)-L-phenylalanylaminomethyl] phosphinic acid Synthesis in analogy to Example 1 from N,N'-bis(L-phenylalanyl-aminomethyl)phosphinic acid hydrochloride and 2S-(1,1-dimethylethylsulfonylmethyl)-3-(1-naphthyl) propionic acid (J. Med. Chem. 31 (1988) 1839).
MS (FAB): 1047 (M+Na)$^+$, 1025 (M+H)$^+$

EXAMPLE 5

N,N'-Bis(L-valyl-aminomethyl)phosphinic acid hydrochloride 2.4 g (4.6 mmol) of bis(tert.-butoxycarbonyl-L-valylaminomethyl)phosphinic acid were stirred in a 3N solution of HCl in methanol/dioxane (1:1) at room temperature for 3 h. The volatile constituents of the solution were removed in vacuo, and the residue was taken up in methanol and precipitated in 200 ml of diethyl ether.
Yield: 80%;
$^1$H-NMR (270 MHz/DMSO/TMS): 0.95 (d, 12H); 2.08 (m, 2H); 3.31 (s, broad, 4H); 3.69 (d, 2H); 8.17 (s, broad, 6H); 8.68 (s, broad, 2H);
MS (FAB/triethanolamine/LiCl): 335 (M+2Li—H)$^+$

EXAMPLE 6

N,N'-Bis(tert.-butoxycarbonyl-L-phenylalanyl-L-valylaminomethyl)phosphinic acid 39 mg (0.34 mmol) of NEM were added dropwise at 0° C. to 91 mg (0.34 mmol) of N-tert.-butoxycarbonylphenylalanine and 109 mg (0.34 mmol) of TBTU dissolved in 50 ml of acetonitrile. The mixture was stirred at 0° C. for 10 minutes and then 50 mg (0.15 mmol) of N,N'-bis(L-valyl-aminomethyl)phosphinic acid hydrochloride dissolved in 30 ml of acetonitrile-/water (1:1) and 32 mg (0.25 mmol) of NEM was added dropwise. The cooling was removed, and the mixture was stirred at room temperature for 3 h. The solvent was removed in a rotary evaporator, and the residue was purified by chromatography on silica gel ($CH_2Cl_2$/methanol/-AcOH/$H_2O$: 100/10/1/1).
Yield: 63%;
$^1$H-NMR (270 MHz/DMSO/TMS): 0.85 (dd, 12H); 1.28 (s, 18H), 2.01 (m, 2H); 2.72 (t, 2H); 2.98 (d, 2H) 3.13 (s, broad, 4H); 4.13–4.32 (m, 4H); 7.05 (d, 2H); 7.11–7.3 (m, 10H); 7.83 (s, broad, 2H); 8.21 (s, broad, 2H);
MS (FAB, triethanolamine, LiCl): 829 (M+2Li—H)$^+$; 823 (M+Li)$^+$

EXAMPLE 7

N,N'-Bis(L-phenylalanyl-L-valyl-aminomethyl) phosphinic acid hydrochloride

Synthesis in analogy to Example 5 from 30 mg of N,N'-bis(tert.-butoxycarbonyl-L-phenylalanyl-L-valyl-aminomethyl)phosphinic acid.
Yield: 84%; $^1$H-NMR (270 MHz/DMSO/TMS): 0.90 (d, 12H); 1.97 (m, 2H); 2.91 (dd,2H); 3.19 (dd, 2H); 3.35 (s, broad, 4H); 4.17 (t, broad, 2H); 4.28 (t, 2H); 7.20–7.48 (m, 10H); 8.13 (s, broad, 6H); 8.60 (d, 2H);
MS (FAB/triethanolamine/LiCl): 629 (M+2Li-H)$^+$; 623 (M+Li)$^+$

EXAMPLE 8

N,N'-Bis (2S—((1,1-dimethylethylsulfonylmethyl)-3-( 1-naphthyl) propionyl)-L-valylaminomethyl) phosphinic acid Synthesis in analogy to Example 4 from N,N'-bis(L-valylaminomethyl)phosphonic acid hydrochloride.
Yield: 35%;
$^1$H-NMR (270 MHz/DMSO/TMS): 0.85 (d, 12H); 1.12 (s, 18H); 1.98 (m, 2H; 2.87 (d, 2H); 3.0–3.7 (m, about 12H); 4.18 (m, 2H); 7.29–7.93 (m, 14H); 8.19 (d, 2H); 8.28 (d, 2H);
MS (FAB/triethanolamine/LiCl): 967 (M+2Li-H)$^+$; 961 (M+Li)$^+$

EXAMPLE 9

N,N'-Bis(2S-((1,1-dimethylethylsulfonylmethyl)-3-phenylpropionyl)-L-valyl-aminomethyl)phosphinic acid Synthesis in analogy to Example 4 from N,N'-bis(L-valylaminomethyl)phosphinic acid hydrochloride and 2S-(1,1-dimethylethylsulfonylmethyl)-3-phenylpropionic acid (J. Med. Chem. 31 (1988) 1839).
Yield: 43%;
MS (FAB/triethanolamine/LiCl): 867 (M+2Li—H)$^+$; 861 (M+Li)$^+$

EXAMPLE 10

N,N'-Bis (tert.-butoxycarbonyl-glycyl-L-valyl-aminomethyl)phosphinic acid

Synthesis in analogy to Example 6 from N,N'-bis(L-valylaminomethyl)phosphinic acid hydrochloride and tert.-butoxycarbonylglycine.

Yield: 71%;

MS (FAB/triethanolamine/LiCl): 649 (M+2Li—H)$^+$; 643 (M+Li)$^+$

EXAMPLE 11

N,N'-Bis(glycyl-L-valyl-aminomethyl)phosphinic acid hydrochloride

Synthesis in analogy to Example 5 from N,N'-bis(tert.-butoxycarbonyl-glycyl-L-valylaminomethyl)phosphinic acid.

Yield: 79%;

MS (FAB/triethanolamine/UCl): 449 (M+2Li—H)$^+$; 443 (M+Li)$^+$

EXAMPLE 12

N,N'-Bis(tert.-butoxycarbonyl-D-phenylalanyl-L-valylaminomethyl)phosphinic acid

Synthesis in analogy to Example 6 fron N,N'-bis(L-valylaminomethyl)phosphinic acid hydrochloride and tert.-butoxycarbonyl-D-phenylalanine.

Yield: 55%;

MS (FAB, triethanolamine, LiCl): 829 (M+2Li—H)$^+$; 823

EXAMPLE 13

N,N'-Bis(D-phenylalanyl-L-valyl-aminomethyl)phosphinic acid hydrochloride

Synthesis in analogy to Example 5 from N,N'-bis(tert.-butoxycarbonyl-D-phenylalanyl-L-valylaminomethyl)phosphinic acid. acid.

Yield: 85%;

MS (FAB, triethanolamine, LiCl): 629 (M+2Li—H)$^+$; 623 (M+Li)$^+$

EXAMPLE 14

N,N'-Bis(tert.-butoxycarbonyl-L-methionyl-L-valyl-aminomethyl)phosphinic acid

Synthesis in analogy to Example 6 from N,N'-bis(L-valyl-aminomethyl)phosphinic acid hydrochloride and tert.-butoxycarbonyl-L-methionine.

Yield: 58%;

MS (FAB, triethanolamine, LiCl): 797 (M+2Li—H)$^+$; 791 (M+Li)$^+$

EXAMPLE 15

N,N'-Bis(L-methionyl-L-valyl-aminomethyl)phosphinic acid hydrochloride

Synthesis in analogy to Example 5 from N,N'-bis(tert.-butoxycarbonyl-L-methionyl-L-valylaminomethyl) phosphinic acid.

Yield: 75%;

MS (FAB, triethanolamine, LiCl): 597 (M+2Li—H)$^+$; 591 (M+Li)$^+$

EXAMPLE 16

N,N'-Bis(tert.-butoxycarbonyl-L-tryptyl-L-valyl-aminomethyl)phosphinic acid

Synthesis in analogy to Example 6 from N,N'-bis(L-valyl-aminomethyl)phosphinic acid hydrochloride and tert.-butoxycarbonyl-D-tryptophan.

Yield: 44%;

MS (FAB, triethanolamine, LiCl): 907 (M+2Li—H)$^+$; 901 (M+Li)$^+$

EXAMPLE 17

N,N'-Bis(L-tryptyl-L-valyl-aminomethyl)phosphinic acid hydrochloride

Synthesis in analogy to Example 5 from N,N'-bis(tert.-butoxycarbonyl-L-tryptyl-L-valylaminomethyl)phosphinic acid.

Yield: 75%;

MS (FAB, triethanolamine, LiCl): 707 (M+2Li—H)$^+$; 701 (M+Li)$^+$

EXAMPLE 18

N,N'-Bis(tert.-butoxycarbonyl-L-isoleucyl-aminomethyl)phosphinic acid

Synthesis in analogy to Example 1b from tert.-butoxycarbonyl-L-isoleucine and bis(aminomethyl)phosphinic acid hydrochloride.

Yield: 46%;

MS (FAB, triethanolamine, LiCl): 563 (M+2Li—H)$^+$; 557 (M+Li)$^+$

EXAMPLE 19

N,N'-Bis(L-isoleucyl-aminomethyl)phosphinic acid hydrochloride

Synthesis in analogy to Example 5 from N,N'-bis(tert.-butoxycarbonyl-L-isoleucyl-aminomethyl)phosphinic acid.

Yield: 82%;

MS (FAB, triethanolamine, LiCl): 363 (M+2Li—H)$^+$; 357 (M+Li)$^+$

EXAMPLE 20

N,N'-Bis(2S-((1,1-dimethylethylsulfonylmethyl)-3-(1-naphthyl)propionyl)-L-isoleucylaminiomethyl)phosphinic acid Synthesis in analogy to Example 4 from N,N'-bis(L-isoleucylaminomethyl)phosphinic acid hydrochloride.

Yield: 42%;

MS (FAB/triethanolamine/LiCl): 995 (M+2Li—H)$^+$; 989 (M+Li)$^+$

EXAMPLE 21

N,N'-Bis(tert.-butoxycarbonyl-L-asparaginyl-aminomethyl)-phosphinic acid

Synthesis in analogy to Example 1b from tert.-butoxycarbonyl-L-asparagine and bis(aminomethyl)phosphinic acid hydrochloride.

Yield: 59%;

MS (FAB): 597 (M+2Na—H)$^+$; 575 (M+Na)$^+$

EXAMPLE 22

N,N'-Bis(L-asparaginyl-aminomethyl)-phosphinic acid hydrochloride

Synthesis in analogy to Example 5 from N,N'-bis(tert.-butoxycarbonyl-L-asparaginylaminomethyl)phosphinic acid.

Yield: 74%;

MS (FAB, triethanolamine, LiCl): 365 (M+2Li—H)$^+$

EXAMPLE 23

N,N'-Bis(2S-((1,1-dimethylethylsulfonylmethyl)-3-(1-naphthyl)propionyl)-L-asparaginylaminomethyl) phosphinic acid Synthesis in analogy to Example 4 from N,N'-bis(L-asparaginylaminomethyl)phosphinic acid hydrochloride.

Yield: 23%;

MS (FAB/triethanolamine/LiCl): 997 (M+2Li—H)$^+$; 991 (M+Li)$^+$

EXAMPLE 24

Monoethyl bis[N-benzyl-(amino-phenyl)methyl] phosphinate 1.65 g (25 mmol) of anhydrous $H_3PO_2$ in 10 ml of absolute ethanol were added to 10 g (50 mmol) of (N-benzyl)benzylimine in 50 ml of absolute ethanol. The mixture was then boiled under reflux with exclusion of moisture for 6 h. It was filtered and crystallized at 0° C. (1:1 mixture of diastereomers).

Yield: 8%;

m.p.: 134°–136° C.;

$^1$H-NMR (270 MHz/CDCl$_3$/TMS): 0.8 (t, 3H); 3.15–3.82 (m, 6H); 4.28 & 4.32 (each d, total: 2H, $J_{PH}$=16 Hz); 7.17–7.41 (m, 20H, Ar—H)

MS (FAB, trifluoroacetic acid, LiCl): 491 (M+Li)$^+$ 485 (M+H)$^+$

EXAMPLE 25

Bis[N-benzyl-(amino-phenylmethyl]phosphinic acid 0.1 g of anhydrous AlCl$_3$ was added to 10 g (50 mmol) (N-benzyl)benzylimine and 1.65 g (25 mmol) of anhydrous $H_3PO_2$ in 60 ml of absolute toluene. The mixture was then boiled under reflux with exclusion of moisture for 6 h. It was washed three times with water and dried over MgSO$_4$, and the solvent was evaporated off. The residue was purified by chromatography on silica gel (1:1 mixture of diastereomers).

Yield: 8%; $^1$H-NMR (270 MHz/CDCl$_3$/TMS): 3.44–3.72 (dd, 4H); 4.09 (d, 2H, $J_{PH}$=16 Hz); 7.03–7.45 (m, 20H);

MS (FAB): 469 (M+2Li—H)

EXAMPLE 26

Bis[N-Triphenylmethyl-(1-amino-2-phenyl)ethyl] phosphinic acid 6 g (0.05 mol) phenyl acetaldehyde and 13 g (0.05 mol) triphenylmethylamine were dissolved in 200 ml absolute toluene, 5 ml absolute glacial acetic acid were added and then boiled under azeotropic removal of water for 10 h. The phenylacetaldehyde-triphenylmethylimine was purified by chromatography on silica gel.

Yield: 74%;

MS (DCl): 362 (M+H)$^+$

Bis [N-triphenylmethyl-(1-amino-2-phenyl)ethyl]-phosphinic acid was synthesized in analogy to example 25 from $H_3PO_2$ and phenylacetaldehyde triphenylmethylimin (mixture of diastereomers).

Yield: 5%

MS (FAB, triethanolamine, LiCl): 801 (M+2Li—H)$^+$; 795 (M+Li)$^+$

EXAMPLE 27

Bis(1-amino-2-phenyl)ethylphosphinic acid hydrochloride 6.5 g (0.6 mmol) bis[N-triphenylmethyl)-(1-amino-2-phenyl)ethyl]phosphinic acid were dissolved in 100 ml methanolic HCl (approx. 3N) and stirred for 10 h at 30° C. The solvent was removed in a rotary evaporator and 4 times with ethanol coevaporated. It was dissolved in water and the water phase was extracted 2 times with CH$_2$Cl$_2$, the solvent was removed in a rotary evaporator and the product was dried (mixture of diastereomers).

Yield: 70%;

(FAB, triethanolamine, LiCl): 317 (M+2Li—H)$^+$; 311 (M+Li)$^+$

EXAMPLE 28

N,N'-Bis(tert.-butoxycarbonyl-L-valyl-1-amino-2-phenyl)ethylphosphinic acid

Synthesis in analogy to example 1b from tert.-butoxycarbonyl-L-valin and bis(1-amino-2-phenyl) ethylphosphinic acid hydrochloride (mixture of diastereomers).

Yield: 48%;

(FAB, triethanolamine, LiCl): 715 (M+2Li—H)$^+$; 709 (M+Li)$^+$

EXAMPLE 29

N,N'-Bis(L-valyl-1-amino-2-phenyl)ethylphosphinic acid

Synthesis in analogy to example 5 from N,N'-bis(tert.-butoxycarbonyl-L-valyl-1-amino-2phenyl)ethylphosphinic acid (mixture of diastereomers).

Yield: 75%;

MS (FAB, triethanolamine, LiCl): 515 (M+2Li—H)$^+$; 509 (M+Li)$^+$

EXAMPLE 30

N,N'-Bis(2S-((1,1-dimethylethylsulfonylmethyl)-3-(1-naphthyl)-propionyl-L-valyl-1-amino-2-phenyl) ethylphosphinic acid Synthesis in analogy to example 4 from N,N'-bis(L-valyl-1-amino-2-phenyl)-ethylphosphinic acid (mixture of diastereomers).

Yield: 41%;

(FAB, triethanolamine, LiCl): 1174 (M+2Li—H)$^+$

EXAMPLE 31

N,N'-Bis-(benzyloxycarbonyl-L-valyl-1-aminomethyl)-phosphinic acid

Synthesis in analogy to example 1b from benzyloxycarbonyl-L-valin and bis(aminomethyl) phosphinic acid hydrochloride.

Yield: 66%;

MS (FAB): 635 (M+2Na—H)$^+$; 613 (M+Na)$^+$

EXAMPLE 32

N,N'-Bis-(benzyloxycarbonyl-L-valyl-1-amino2-phenyl)ethylphosphinic acid

Synthesis in analogy to example 1b from benzyloxycarbonyl-L-valin and bis(1-amino-2-phenyl)ethylphosphinic acid hydrochloride (mixture of diastereomers).

Yield: 39%;

(FAB, triethanolamine, LiCl): 783 (M+2Li—H)$^+$; 777 (M+Li)$^+$

We claim:

1. A compound of the formula I

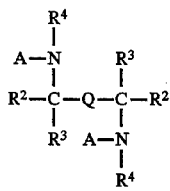
(I)

wherein:

Q is a radical of the formula IIa;

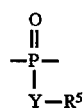
(IIa)

in which:

Y is oxygen;

$R^5$ is hydrogen, $(C_1-C_6)$-alkyl, $(C_6-C_{10})$-aryl, $(C_7-C_{20})$-arylalkyl, which may be substituted by alkoxy, or glyceryl or is a residue of a phosphate prodrug, or acyl-oxyalkyl;

A is a radical of the formula (IV):

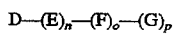
(IV)

in which:

E, F or G is Gly, Ala, Val, Leu, Ile, Nva, Nle, Phe, Tyr, Asp or Glu;

D is $R^1$ or a radical of the formula (VI):

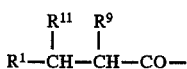
(VI)

and n+o+p is 1;

$R^1$ is hydrogen, $(C_1-C_6)$-alkylsulfonyl, $(C_8-C_{10})$-aryl-$(C_1-C_2)$-alkyl, triphenylmethyl, $(C_1-C_6)$-alkoxycarbonyl or $(C_6-C_{10})$-aryl-$(C_1-C_2)$-alkoxycarbonyl;

$R^2$ is hydrogen, phenyl or benzyl;

$R^3$, $R^4$ and $R^{11}$ are hydrogen and $R^9$ is hydrogen, n-propyl, isopropyl, n-butyl, sec.-butyl, isobutyl, benzyl, carboxymethyl, carboxyethyl, 1-naphthylmethyl, 2-napthylmethyl, 2-(methylthio)ethyl, 2-(methylsulfinyl)ethyl, 2-(methylsulfonyl)ethyl, indol-2-yl-methyl or indol-3-yl-methyl;

or a physiologically tolerated salt thereof.

2. A compound of the formula I

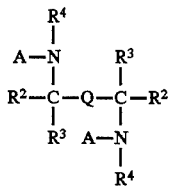
(I)

wherein:

Q is radical of the formula IIa

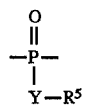
(IIa)

in which:

Y is oxygen;

$R^5$ is hydrogen or $(C_1-C_4)$-alkyl;

A is a radical of the formula (IV):

ti D—(E)$_n$—(F)$_o$—(G)$_p$+tm (IV)

in which:

E, F or G is Val, Phe, Ile or Asp;

D is $R^1$ or a radical of the formula (VI):

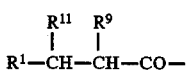
(VI)

and n+o+p is 1;

$R^1$ is hydrogen, $(C_1-C_6)$-alkylsulfonyl, phenyl-$(C_1-C_2)$-alkyl, triphenylmethyl, $(C_1-C_6)$-alkoxycarbonyl or phenyl-$(C_1-C_2)$-alkoxycarbonyl;

$R^2$ is hydrogen, phenyl or benzyl;

$R^3$, $R^4$ and $R^{11}$ are hydrogen; and $R^9$ is hydrogen, isopropyl, sec.-butyl, benzyl, carboxymethyl, 1-napthylmethyl, 2-(methylthio)ethyl or indol-2-yl-methyl;

or a physiologically tolerated salt thereof.

* * * * *

UNITED STATES PATENT AND TRADEMARK OFFICE
CERTIFICATE OF CORRECTION

PATENT NO. : 5,629,431

DATED : May 13, 1997

INVENTOR(S) : Karl-Heinz BUDT et al.

It is certified that error appears in the above-indentified patent and that said Letters Patent is hereby corrected as shown below:

Claim 1, column 38, line 2, after "hydrogen", insert --;--.

Claim 2, column 38, line 20, after "Q is", insert --a--.

Claim 2, column 38, line 31, "ti D-(E)$_n$ -(F).-(G)$_p$+tm (IV)" should read --D-(E)$_n$ -(F).-(G)$_p$ (IV)--.

Claim 2, column 38, line 41, "($C_1$ -$C_6$)-alkylsuifonyl" should read --($C_1$ -$C_6$)-alkylsulfonyl--.

UNITED STATES PATENT AND TRADEMARK OFFICE
CERTIFICATE OF CORRECTION

PATENT NO. : 5,629,431

DATED : May 13, 1997

INVENTOR(S) : Karl-Heinz BUDT et al.

It is certified that error appears in the above-indentified patent and that said Letters Patent is hereby corrected as shown below:

Claim 2, column 38, line 42, "triphenymethyl" should read --triphenylmethyl--.

Signed and Sealed this

Twenty-first Day of October 1997

Attest:

BRUCE LEHMAN

Attesting Officer

Commissioner of Patents and Trademarks